US011929149B2

(12) United States Patent
Quiroz Zarate et al.

(10) Patent No.: US 11,929,149 B2
(45) Date of Patent: Mar. 12, 2024

(54) SYSTEMS AND METHODS FOR GENOMIC ANALYSIS

(71) Applicant: ARC BIO, LLC, Cambridge, MA (US)

(72) Inventors: Alejandro Quiroz Zarate, Cambridge, MA (US); Roberto Olivares-Amaya, Somerville, MA (US); Thomas James Watson, Jr., Auburndale, MA (US); Helen Cecile Van Aggelen, Somerville, MA (US); Eduardo Coronado Sroka, Boston, MA (US); Carlos Antonio Angulo Sermeno, San Luis Potosi (MX); Fernando Fimbres Jurado, Leon (MX); Abraham Solis Garcia-Inda, Irapuato (MX); Fernando Fontove Herrera, Iraputo (MX); Pablo G. Coste, Newton, MA (US)

(73) Assignee: ARC BIO, LLC, Cambridge, MA (US)

( * ) Notice: Subject to any disclaimer, the term of this patent is extended or adjusted under 35 U.S.C. 154(b) by 908 days.

(21) Appl. No.: 15/750,350

(22) PCT Filed: Aug. 4, 2016

(86) PCT No.: PCT/US2016/045564
§ 371 (c)(1),
(2) Date: Feb. 5, 2018

(87) PCT Pub. No.: WO2017/024138
PCT Pub. Date: Feb. 9, 2017

(65) Prior Publication Data
US 2020/0090786 A1    Mar. 19, 2020

Related U.S. Application Data

(60) Provisional application No. 62/201,923, filed on Aug. 6, 2015.

(51) Int. Cl.
G16B 30/10 (2019.01)
G16B 5/00 (2019.01)
G16B 25/10 (2019.01)
G16B 50/30 (2019.01)
G16B 45/00 (2019.01)
G16B 40/10 (2019.01)
G16B 30/20 (2019.01)
G16B 40/20 (2019.01)
C12Q 1/6869 (2018.01)

(52) U.S. Cl.
CPC .......... G16B 30/10 (2019.02); C12Q 1/6869 (2013.01); G16B 5/00 (2019.02); G16B 25/10 (2019.02); G16B 30/20 (2019.02); G16B 40/10 (2019.02); G16B 40/20 (2019.02); G16B 45/00 (2019.02); G16B 50/30 (2019.02)

(58) Field of Classification Search
CPC .................................................... G16B 30/10
See application file for complete search history.

(56) References Cited

U.S. PATENT DOCUMENTS

| | | |
|---|---|---|
| 5,750,341 A | 5/1998 | Macevicz |
| 6,306,597 B1 | 10/2001 | Macevicz |
| 7,115,400 B1 | 10/2006 | Adessi |
| 7,211,390 B2 | 5/2007 | Rothberg |
| 7,232,656 B2 | 6/2007 | Balasubramanian |
| 7,244,559 B2 | 7/2007 | Rothberg |
| 7,264,929 B2 | 9/2007 | Rothberg |
| 7,323,305 B2 | 1/2008 | Leamon |
| 7,948,015 B2 | 5/2011 | Rothberg |
| 8,209,130 B1 | 6/2012 | Kennedy |
| 2008/0160580 A1 | 7/2008 | Adessi |
| 2008/0222114 A1* | 9/2008 | Schreiber ........... G06Q 30/0273 |
| 2008/0286795 A1 | 11/2008 | Kawashima |
| 2009/0026082 A1 | 1/2009 | Rothberg |
| 2014/0022911 A1 | 1/2014 | Sandick et al. |
| 2014/0025593 A1 | 1/2014 | Dolin |
| 2014/0229114 A1 | 8/2014 | Singh |
| 2014/0255931 A1 | 9/2014 | Porreca |
| 2015/0019947 A1 | 7/2015 | Hawking |
| 2015/0199475 A1 | 7/2015 | Kural |

FOREIGN PATENT DOCUMENTS

WO    2009046445 A1    4/2009

OTHER PUBLICATIONS

Li et al., SOAPindel: Efficient identification of indels from short paired reads, 2013, Genome Research, 23, p. 195-200 (Year: 2013).*
Nielsen et al., Genotype and SNP calling from next-generation sequencing data, 2011, Nat Rev Genet., 12(6), p. 443-451 (Year: 2011).*
Dilthey et al., Improved genome inference in the MHC using a population reference graph, Nature Genetics, 2015, 47(6), p. 682-668 and supplemental (Year: 2015).*
Homer et al., BFAST: An Alignment Tool for Large Scale Genome Resequencing, 2009, PLos ONE, 4(11), p. 1-12 (Year: 2009).*
Ames et al., Scalable metagenomic taxonomy classification using a reference genome database, 2013, 29(18), p. 2253-2260 (Year: 2013).*
Coll et al., A robust SNP barcode for typing Mycobacterium tuberculosis complex strains, 2014, Nature Communications, 5:4812, p. 1-5 (Year: 2014).*
AMD, The AMD Opteron processor is the ideal solution for High Performance Computing, 2012, AMD, p. 1-2 (Year: 2012).*
International Search Report and Written Opinion from parent application No. PCT/US2016/045564, dated Jan. 13, 2017, 20 pages.
Anonymous: SAM, Internet Citation, Mar. 11, 2015 (Mar. 11, 2015), XP002771304, Retrieved from the Internet: URL:https://web.archive.org/web/20150311045750/http://davetang.org/wiki/tiki-index.p hp?page=SAM [retrieved on Jun. 22, 2017]. (5 pages).

(Continued)

Primary Examiner — Kaitlyn L Minchella
(74) Attorney, Agent, or Firm — Quarles & Brady LLP

(57) ABSTRACT

Provided herein are methods for aligning raw genetic sequence data generated by a sequencing device. Also provided herein are methods and systems for quantifying the probability that possible alignments for one or more read pairs are correct, for calling known variants, and for detecting novel structural variants.

22 Claims, 9 Drawing Sheets

Specification includes a Sequence Listing.

(56) References Cited

OTHER PUBLICATIONS

Li Heng et al: Mapping Short DNA Sequencing Reads and Calling Variants Using Mapping Quality Scores11 Genome Research, Cold Spring Harbor Laboratory Press, US, vol. 18, Jan. 1, 2008 (Jan. 1, 2008), pp. 1851-1858, XP001503357, ISSN: 1088-9051, DOI: 10.1101/GR.078212.108 [retrieved on Aug. 19, 2008]. (9 pages).
European Search Report from European Patent Application No. 16833874.7, dated Dec. 5, 2018. (8 pages).
Gudmundsson, J., et al. "Genome-wide association and replication studies identify four variants associated with prostate cancer susceptibility." Nature genetics 41.10 (2009): 1122.
Margulies, M., et al. "Genome sequencing in microfabricated high-density picolitre reactors." Nature 437.7057 (2005): 376-380.
Out, A. A., et al. "Deep sequencing to reveal new variants in pooled DNA samples." Human mutation 30.12 (2009): 1703-1712.
Soni, G. V. et al. "Progress toward ultrafast DNA sequencing using solid-state nanopores." Clinical chemistry 53.11 (2007): 1996-2001.
Turner, E. H., et al. "Massively parallel exon capture and library-free resequencing across 16 genomes." Nature methods 6.5 (2009): 315-316.
European Patent Office, Office Action for application 16833874.7, dated Dec. 5, 2019, 4 pages.
Philippe et al., Querying large read collections in main memory: a versatile data structure, BMC Bioinformatics 2011, 12:242.

\* cited by examiner

```
Coor        12345678901234 567890123456789012345
ref         AGCATGTTAGATAA**GATAGCTGTGCTAGTAGGCAGTCAGGCCAT ——— 501   (SEQ ID NO:2)
                          |  / - |
bub         GCCTA    C                GCTGCTGCT
id          rs14     rs16             rs22 ——— 502
                                           503

+r001/1     TTAGATAAAGGATA*CTG  (SEQ ID NO:3)
+r002              aaaAGATAA*GGATA  (SEQ ID NO:4)
+r003                    gcctaAGCTAA  (SEQ ID NO:5)
+r004                       ATAGCT............TCAGC
                                            gctgct
-r003                                       TAGGC        504
-r001/2                                              CAGCGGCAT
```

```
@HD  VN:1.5  SO:coordinate
@SQ  SN:ref  LN:45
r001  99   ref   7   30  8M2I4M1D3M  =  37   39  TTAGATAAAGGATACTG    (SEQ ID NO:6)       NL:Z:rs14,rs16;NN:1:2
r002  0    ref   9   30  2S7M1P1I4M  *   0    0  AAAAGATAAGGATA       (SEQ ID NO:7)    *  VL:Z:rs14;GD:Z:2+2S1B6M1P1I4M;
                                                                                          VN:i:1;NN:i:1;NL:Z:rs16
r003  0    ref   9   30  11M         *   0    0  GCCTAAGCTAA          (SEQ ID NO:8)    *  SA:Z:ref,29,-,11M,17,0;
                                                                                          VL:Z:rs14,rs16; VV:Z:rs14
r004  0    ref   16  30  6M14N5M     *   0    0  ATAGCTTCAGC                           *  GD:Z:5B2M1B3M;GR:Z:0-6,0-3
r003  2064 ref   29  17  11M         =   7  -39  CAGCGGCAT            (SEQ ID NO:9)    *  SA:Z:ref,9,+,11M,30,1;
                                                                                          VL:Z:rs22;VN:i:1; VV:Z:rs22
r001  147  ref   37  30  9M          =   7  -39  CAGCGGCAT            (SEQ ID NO:10)   *  GD:Z:3+6B5M;GR:Z:4-15
                                                                                          NM:i:1
```

FIG. 5

Sequence k-mer-ization

801 —— A A T G A A C A A T G (SEQ ID NO:11)

802
- AATGAACAATG
- AATGAACAATG
- AATGAACAATG
- AATGAACAATG
- AATGAACAATG
- AATGAACAATG
- AATGAACAATG
- AATGAACAATG

*FIG. 8A*

Offset normalization

Reference sequence    G G G G C A G G T A A T G A A C G A C G G (SEQ ID NO:12)

AATGAACAATG    (SEQ ID NO:11)

803 ——
- AATGAACAATG
- AATGAACAATG
- AATGAACAATG

*FIG. 8B*

SYSTEMS AND METHODS FOR GENOMIC ANALYSIS

CROSS-REFERENCE

This application is a U.S. 371 National Phase Entry of PCT/US2016/045564, filed Aug. 4, 2016, which claims the benefit of U.S. Provisional Application No. 62/201,923, filed Aug. 6, 2015, each of which is incorporated herein by reference.

BACKGROUND

Biological sequencing is the process of determining the precise order of monomers (e.g., nucleotides or amino acids) within biomolecules such as DNA, RNA, proteins, and other polymers. The rapid development of sequencing methods and instruments can significantly advance biomedical studies. For example, next-generation nucleic acid sequencing technologies can provide a new paradigm for a low-cost, high-throughput sequencing process. Next-generation sequencing technologies can parallelize the sequencing process in order to simultaneously produce thousands or millions of nucleotide sequences resulting in massive amounts of information. The precision of sequencing can also be enhanced significantly by next-generation sequencing technologies. Such technologies can enable researchers to collect large amounts of high-precision sequence data within a shorter time. Whole genome DNA and RNA sequences have become a routine for genetic testing and for disease diagnosis and treatment.

Typically, genomic data can be archived in repositories, for example, individual repositories (e.g., those associated with laboratories generating the genomic data) or public sequence repositories, which archive data received from various laboratories in a central repository. Storage of such large volumes of data requires the repositories to have large storage disks having huge volumes of storage capacity. Further, with the advances in the research, the amount of incoming genomic data may also increase, thereby increasing maintenance costs and requirements for additional storage space. Furthermore, since the genomic data can be utilized for future references, the genomic data may be archived in a compressed form so as to allow decompression and retrieval without any loss of information.

SUMMARY

Disclosed herein is a method for aligning raw genetic sequence data generated by a sequencing device, the method comprising: (a) retrieving raw genetic sequence data generated by a sequencing device; and (b) aligning said raw genetic sequence data generated by a sequencing device to a location on genome variation map, wherein the genome variation map comprises alternate paths. In some embodiments, the mapping is performed by graph alignment. In some embodiments the graph alignment uses a single graph. In some embodiments the mapping is performed using a gapped alignment. In some embodiments the mapping is performed using a semi-gapped alignment. In some embodiments further comprising accumulating a number of times a particular path from the alternative paths is mapped to in the mapping step.

Disclosed herein is a method to quantify the probability that possible alignments for one or more read pairs are correct, in which the probabilities that possible alignments for a subset of read pairs are correct are calculated as a function of the probabilities that the individual reads are aligned correctly and an estimated probability for observing the alignment features of the pair, including, but not limited to, the distance between the aligned reads and the alignment orientation of both reads of the pair. In some embodiments, the probability that possible alignments for one or more read pairs are correct can be additionally scored based on the alignment features of one or more other read pairs in the subset, which can be read pairs with the same barcode.

Disclosed herein is a method to quantify the probability that possible alignments for one or more reads are correct, in which the probabilities that possible alignments for a subset of reads are correct are calculated as a function of the probability that the individual read's alignment is correct and the probability of observing the alignment features of other reads in the subset, which can be reads with the same barcode.

Disclosed herein are systems and methods for improved variant calling by combining graph reference alignment with novel variant or structural variant detection. A method for detecting variants includes a) obtaining a plurality of sequence reads, b) aligning them with a graph reference, c) identifying reads that can indicate the presence of variation or structural variation and passing them to a variant caller, either directly or indirectly (e.g. written to file first). In some embodiments, a subset of novel detected variants can be added automatically to the reference and this updated reference can then be used for another alignment. In some embodiments, a subset of reads that indicate the presence of variation or structural variation are identified while the alignment step is in progress (that is, not all sequence reads have been aligned yet) and written to file or passed to a variant caller. In this manner there is no step needed to scan through all aligned reads before variant calling. The novel variant detection can then be carried out while the graph reference alignment is in progress or subsequently.

Disclosed herein is a system to characterize the alignment of a sequence read with a graph reference in a format that is compatible with the format used for reads aligned with a linear reference, the system comprising a) a receiving module configured to receive a graph alignment of a read, wherein the graph reference sequence comprises known variants represented by variant paths relative to a linear reference sequence; and b) a reporting module that characterizes the graph alignment of the read by reporting the start of its alignment relative to the coordinate of the reference sequence and, if the read aligns to a variant path, a read tag that represents an identification number of the variant. In some cases, a read flag can be set if the read aligns to a variant. In some cases, the reporting module further specifies a read tag that indicates the start of the aligned read relative to the coordinate of the variant path. In some cases, the reporting module further specifies a read tag that indicates the start and the end of the aligned read relative to the coordinate of the variant path. In some embodiments, the reporting module specifies a read tag that contains a set of alignment scores relative to the variant path. In some embodiments, the alignment of the read with a graph reference can be translated back to the coordinate of the linear reference.

Disclosed here is a method to generate a single phased alternate sequence path, the method comprising: obtaining a reference sequence; retrieving correlated loci on a reference sequence that are alternate to the reference sequence, and generating a single phased alternate sequence path comprising the correlated loci. In some embodiments the correlated loci are from two or more subjects. In some embodiments the correlated loci are a set of different sequences which map to more than one location on the reference sequence. In some embodiments the at least two of the set of different sequences are phased. In some embodiments the method further comprises indexing said phased set of the at least two of the set of different sequences.

Disclosed herein is a method to index a reference sequence with alternate paths, the method comprising: (a) receiving a reference sequence; (b) receiving alternate sequences which are anchored in said reference sequence; (c) generating a plurality of k-mers of said reference sequence and alternate sequences in less than or equal to two hours; and (d) indexing the reference sequence with alternate paths using said k-mers. In some embodiments the reference sequence is a human reference genome. In some embodiments the reference sequence is a non-human reference genome. In some embodiments the generating uses a linear reference coordinate system to directly index the k-mers. In some embodiments the generation does not involve assigning node id's, edges, or paths.

Disclosed herein is a method to index a reference sequence with alternate paths, the method comprising: (a) receiving a reference sequence; (b) receiving alternate sequences which are anchored in to said reference sequence; (c) generating an indexed plurality of k-mers of said reference sequence and alternates that fits in less than or equal to 80 gigabytes of computer space; and (d) indexing the reference sequence with alternate paths using said k-mers. In some embodiments the computer space is selected from one or more of disk, ram, or address space. In some embodiments the reference sequence is a human reference genome. In some embodiments the reference sequence is a non-human reference genome. In some embodiments the generating step is performed by directly using a linear reference coordinate system and indexing directly the k-mers of alternates as they appear in that coordinate system. In some embodiments the generating does not involve assigning node id's, edges, or paths.

Disclosed herein is a method to query an index of k-mers in a reference sequence with alternate paths, the method comprising: (a) retrieving an index comprising a plurality of k-mers and locations in a reference sequence containing alternate paths from a reference sequence with alternate paths; and (b) querying said index with k-mers in a reference sequence with alternate paths at the rate of greater than or equal to 69,000 k-mers per second per compute thread. In some embodiments the querying is performed on multiple compute threads at a rate of greater than or equal to 345,000 k-mers per second per compute thread. In some embodiments the number of compute threads is greater than 4.

In some embodiments the number of compute threads is greater than 1, greater than 2, greater than 3, greater than 4 greater than 5, greater than 6, greater than 7, greater than 8, greater than 9, greater than 10, greater than 20, greater than 30, greater than 40, greater than 50, greater than 60, greater than 70, greater than 80, greater than 90, or greater than 100. In some embodiments the querying is performed on multiple compute cores at a rate of greater than or equal to 345,000 k-mers per second per core.

In some embodiments greater than 95% of processor work is dedicated to querying the index. In some embodiments greater than 85% of processor work is dedicated to querying the index. In some embodiments greater than 75% of processor work is dedicated to querying the index. In some embodiments greater than 65% of processor work is dedicated to querying the index.

In some embodiments processor work is work solely dedicated to querying the index. In some embodiments the processor work does not comprise one or more of the group consisting of kernel tasks, memory swaps, or I/O.

In some embodiments the k-mers are a length of at least 10, 20, 30, 40, 50, 60, 70, 80, 90, or 100 nucleotides (nt). In particular embodiments, the k-mers are a length of at least 32.

Disclosed herein is a method to compare sequences, the method comprising: (a) retrieving from a sequencer a read while a sequencing assay is in progress;(b) comparing said read to a sequence while the sequencing assay is in progress; and (c) determining if a specific locus is in said read. In some embodiments the methods further comprise accumulating a count of occurrences of said specific locus.

Disclosed herein are methods for phasing loci in a reference genome that have alternate sequences, the method comprising: (a) retrieving an accumulation of a number of occurrences multiple alternative path in a sequence, wherein each multiple alternative path comprises loci; and (b) grouping loci from different alternate paths based on the accumulation abundance counts for the multiple alternative paths; and (c) phasing the loci based upon common groupings. Common groupings can refer to reads that are linked as paired ends, mate pairs, or any other sequence data generated from a single strand of genetic material and separated by a distance.

Disclosed herein are methods to compare sequences, the method comprising: (a) retrieving from a sequencer a read while a sequencing assay is in progress; (b) encrypting said read while the sequencing assay is in progress (c) comparing without decrypting said read to a reference sequence. In some embodiments the reference sequence is a genome variation map. In some embodiments the reference sequence is a reference human genome. In some embodiments the reference sequence is a non-human reference genome.

Disclosed herein are methods to compare sequences, the method comprising: (a) retrieving from a sequencer a read while the sequencing assay is in progress; (b) encrypting said read while the sequencing assay is in progress; and (c) transmitting said encrypted read to a processing device. In some embodiments the method further comprises decrypting said encrypted read. In some embodiments the method further comprises comparing said read to a sequence while the sequencing assay is in progress. In some embodiments the method further comprises transmitting a decrypting key related to the encrypted read.

Disclosed herein are methods to compare sequences, the method comprising: (a) retrieving from a sequencer a read while the sequencing assay is in progress; (b) compressing the said read to a processing device while the sequencing assay is in progress; (c) decompressing said read to a sequence while the sequencing assay is in progress; and (d) comparing said reads to a reference sequence while the sequencing assay is in progress.

Disclosed are systems and methods for calling known variants, the system and methods comprising: (a) retrieving a read; (b) generating a k-mer profile from said read; and (c) querying the k-mer profile to an index of k-mer profiles from a reference sequence with alternate paths to call variants. In some embodiments known variants are identified using at least a single core at a rate greater than or equal to 10 variant calls per second per core.

Disclosed herein is a system for compression of sequencing data, the system comprising: (a) a module for receiving sequencing data; (b) a memory unit for storing said sequencing data; and (c) an encoding module having access to the memory to the sequencing data stored thereon and configured to encode some or all of the sequencing data. In some embodiments the sequencing data is compressed to a level equal or greater than 81.5% of the received sequencing data. In some embodiments the sequencing data comprises fields the fields comprising one of more of: a sequence identifier; base call data; amino acid call data; a line for comments; and quality values for the base call data. In some embodiments the encoding module separates the base call data in the sequencing data from the rest of the sequencing data. In some embodiments the encoding module separates the amino acid call data in the sequencing data from the rest of the sequencing data. In some embodiments a nucleotide base in the base call data is associated with a character corresponding to a nucleotide base: adenine (A), thymine (T), guanine (G), and cytosine (C), and a base which could not be determined is associated with (N). In some embodiments the amino acid call data is associated with a character corresponding to an amino acid.

In some embodiments if a base in the sequencing data cannot be determined then the encoding module does not separate the base call data in the sequencing data from the rest of the sequencing data to encode a read associated with that base. In some embodiments the read associated with the undermined based is compressed as an unseparated read. In some embodiments in a read with a base calls that could not be determined, the position of such base is saved. In some embodiments in all of the reads with base calls that could not be determined, the positions of such bases are saved. In some embodiments at least 90% of the reads with base calls that could not be determined, the positions of such bases are saved. In some embodiments the location of the base is saved in less than 1 byte if length of base is smaller than 256 bases. In some embodiments the location of the base is saved in less than 2 bytes if length is less than 65536 bases. In some embodiments the encoding module save information using delta encoding. In some embodiments the encoding module performs base-4 encoding on the nucleotide-based data. In some embodiments each field of the sequencing data is saved sequentially.

In some embodiments the system disclosed herein has at least two fields that are saved in separate files. In some embodiments at least two different files are saved using different compression algorithms performed on each field. In some embodiments data in a sequence identifier field is compressed using delta encoding. In some embodiments base call data is processed using a Burrows-Wheeler Transform. In some embodiments the processing of the base call data further comprises running run-length encoding and compressing using Huffman Encoding. In some embodiments a line for comments is compressed using delta encoding. In some embodiments an additional line for comments is ignored when the field is empty. In some embodiments quality value data is processed using a Burrows-Wheeler Transform. In some embodiments the processing further comprises running run-length encoding and compressing using Huffman Encoding.

Disclosed herein is a system for compression of sequence alignment map (SAM) data, the system comprising: (a) a memory having stored thereon the SAM data; (b) an encoding module having access to the memory to the SAM data stored thereon and configured to compress the SAM data to a level equal or greater than 80%. In some embodiments the encoding module compresses a query template name in the SAM data using delta encoding. In some embodiments the encoding module compresses a reference sequence name in the SAM data using delta encoding. IES the encoding module compresses a leftmost mapping position in the SAM data using delta encoding. In some embodiments the encoding module compresses a reference name of a mate read in the SAM data using delta encoding. In some embodiments the encoding module compresses a position of a mate read in the SAM data using delta encoding. In some embodiments the encoding module compresses data form a cigar string using Huffman coding method. In some embodiments the encoding module compresses data form a cigar string using a dictionary-based method. In some embodiments encoding module compresses base call data from the SAM data using base 4 encoding. In some embodiments the encoding module compresses quality data from the SAM data. In some embodiments (a) data from the SAM data comprising one or more of a query template name, a reference sequence name, a leftmost mapping position, a reference name of the mate read, and a position of the mate read can each be compressed using delta encoding; (b) data from the SAM data comprising a cigar string can be compressed using Huffman coding or a dictionary-based method; (c) data from the SAM data comprising a base call data can be compressed using base 4 encoding; and (d) data from the SAM data comprising quality data can be compressed. In some embodiments the SAM data is sequentially ordered.

Disclosed herein is a system for compression of variant call format (VCF) data, the system comprising: a memory having stored thereon the VCF data; an encoding module having access to the memory to the VCF data stored thereon and configured to encode the genomic data to a level equal or greater than 95% of the VCF data. In some embodiments the encoding module compresses a query template name in the VCF data using delta encoding. In some embodiments the encoding module compresses a reference sequence name in the VCF data using delta encoding. In some embodiments an encoding module compresses a leftmost mapping position in the VCF data using delta encoding. In some embodiments the encoding module compresses a reference name of a mate read in the VCF data using delta encoding. In some embodiments the encoding module compresses a position of a mate read in the VCF data using delta encoding. In some embodiments the encoding module compresses data form a cigar string using Huffman coding method. In some embodiments the encoding module compresses data form a cigar string using a dictionary-based method. In some embodiments the encoding module compresses base call data from the VCF data using base 4 encoding. In some embodiments the encoding module compresses quality data from the VCF data.

An aspect of the present disclosure provides a method for aligning raw genetic sequence data generated by a sequencing device, the method comprising: (a) obtaining raw genetic sequence data generated by a sequencing device; (b) mapping the raw genetic sequence data generated by the sequencing device to a location on a variation map, wherein the variation map comprises alternate paths; and (c) aligning the raw genetic sequence data generated by the sequencing device according to its location on the variation map.

In some embodiments, the mapping is performed by graph alignment. In some embodiments, the graph alignment uses at least one graph. In some embodiments, the mapping is performed using a gapped alignment. In some embodiments, the mapping is performed using a semi-gapped alignment. In some embodiments, the method further comprises accumulating a number of times that a particular path of the alternative paths is mapped to during the mapping. In some embodiments, the raw genetic sequence data includes one or more read pairs, and wherein probabilities that possible alignments for a subset of read pairs are correct are calculated as a function of (a) probabilities that individual reads of the read pairs are aligned correctly, and (b) an estimated probability of observing alignment features of the read pair, including a distance between the aligned reads in the pair and an alignment orientation of both reads in the pair. In some embodiments, the raw genetic sequence data includes one or more read pairs, and wherein probabilities that possible alignments for a subset of read pairs are correct are calculated as a function of (a) probabilities that individual reads of the read pairs are aligned correctly, (b) an estimated probability of observing alignment features of the pair, including a distance between the aligned reads in the pair and an alignment orientation of both reads in the pair, and (c) an estimated probability of observing possible alignment features of one or more other read pairs in the subset. In some embodiments, probabilities that possible alignments for a subset of reads are correct are calculated as a function of (a) probabilities that individual reads of the read pairs are aligned correctly, and (b) an estimated probability of observing possible alignment features of one or more other reads in the subset.

An aspect of the present disclosure provides a method to identify novel variants, the method comprising: (a) obtaining a plurality sequence reads; (b) aligning the plurality of sequence reads against a graph reference, wherein the graph reference comprises known variants represented by alternate paths; and (c) using a subset of the plurality of sequence reads which abnormally align against one or more alternate paths to identify novel variants.

In some embodiments, the novel variants comprise structural variants. In some embodiments, the subset of the plurality of sequence reads used to identify novel variants aligns abnormally to all alternate paths in the graph reference. In some embodiments, the sequence reads comprise read pairs, and wherein abnormal alignment comprises an aligned read pair orientation different from that of a majority of aligned read pairs. In some embodiments, the sequence reads comprise read pairs, and wherein abnormal alignment comprises an aligned read pair insert length that is significantly smaller or larger than that of the majority of the aligned read pairs. In some embodiments, the insert length is more than 10% larger or smaller than the median insert length of a subset of the aligned reads. In some embodiments, the insert length is more than 50% larger or smaller than the median insert length of a subset of the aligned reads. In some embodiments, the insert length is more than 100% larger or smaller than the median insert length of a subset of the aligned reads. In some embodiments, the insert length is more than 200% larger or smaller than the median insert length of a subset of the aligned reads. In some embodiments, the insert length is more than 300% larger or smaller than the median insert length of a subset of the aligned reads. In some embodiments, the insert length is larger than the 99th or smaller than the 1st percentile of the insert lengths of a subset of the aligned reads. In some embodiments, the insert length is larger than the $98^{th}$ or smaller than the $2^{nd}$ percentile of the insert lengths of a subset of the aligned reads. In some embodiments, the insert length is larger than the 97th or smaller than the 3rd percentile of the insert lengths of a subset of the aligned reads. In some embodiments, the insert length is larger than the 95th or smaller than the 5th percentile of the insert lengths of a subset of the aligned reads. In some embodiments, the insert length is larger than the 90th or smaller than the 10th percentile of the insert lengths of a subset of the aligned reads. In some embodiments, the insert length is larger or smaller than some user-specified value. In some embodiments, the sequence reads comprise read pairs, and wherein abnormal alignment comprises a read pair in which one read is aligned and one read is unaligned. In some embodiments, abnormal alignment comprises a read in which part of the read is clipped. In some embodiments, the portion of the read that is clipped is larger than 10%. In some embodiments, the portion of the read that is clipped is larger than 5%. In some embodiments, the portion of the read that is clipped is larger than 20%. In some embodiments, the portion of the read that is clipped is larger than 30%. In some embodiments, the identified novel variants are variants not previously documented for a target application. In some embodiments, the identified novel variants are variants that are not present in the graph reference. In some embodiments, a subset of the identified novel variants is added automatically to the graph reference to produce an updated graph reference, and wherein the updated graph reference is used for another alignment. In some embodiments, the method further comprises counting a number of reads that align to alternate paths in the graph reference and using the number of reads that align to alternate paths in the graph reference to identify the known variants. In some embodiments, the identified novel variants comprise structural variants. In some embodiments, the known variants are previously documented for a target application. In some embodiments, the novel variants are not previously documented for a target application. In some embodiments, the known variants are variants that are present in the graph reference. In some embodiments, the novel variants are variants that not present in the graph reference. In some embodiments, abnormal alignment comprises one or more of the following: a) an aligned read pair orientation different from that of a majority of aligned read pairs; b) an aligned read pair insert length that is significantly smaller or larger than that of a majority of aligned read pairs; c) a read pair in which one read is aligned and one read is unaligned; d) a read in which a part of the read is clipped; e) a read pair in which an insert length is larger than the $99^{th}$, $98^{th}$, $97^{th}$, $95^{th}$, or 90th percentile or smaller than the $1^{st}$, $2^{nd}$, $3^{rd}$, $5^{th}$, or $10^{th}$ percentile of insert lengths of a subset of aligned read pairs; and f) a read pair in which reads align to different reference sequences. In some embodiments, the different reference sequences are from different chromosomes. In some embodiments, the method further comprises identifying a subset of the identified novel variants that satisfy predefined quality measures or detection certainty measures and adding the subset to the graph reference. In some embodiments, the method further comprises identifying a subset of the identified novel variants that are within a predefined size range and adding the subset to the graph reference. In some embodiments, the method further comprises identifying a subset of the identified novel variants that lie within a predefined region of a genome and adding the subset to the graph reference. In some embodiments, the method further comprises identifying a subset of the identified novel variants that have been detected in one or more pluralities of sequence reads with a frequency greater than a predefined relative or absolute value and adding the subset to the graph reference. In some embodiments, the updated graph reference is used for a subsequent alignment and variant detection. In some embodiments, the graph reference is used and progressively updated in more than one alignment and variant detection. In some embodiments, the graph reference is used and progressively updated in more than one alignment and variant detection on the same computer. In some embodiments, the graph reference is shared and updated among one or more computers. In some embodiments, the graph reference is stored and updated in a central repository and shared among one or more computers. In some embodiments, the known variants or the novel variants comprise intra-species variants. In some embodiments, the known variants or the novel variants comprise inter-species variants.

An aspect of the present disclosure provides a method to detect sequence variants, the method comprising: a) obtaining a plurality of sequence reads; b) creating a batch of aligned reads by a process comprising aligning a subset of the plurality of sequence reads against a graph reference, wherein the graph reference comprises known variants represented by alternate paths; c) identifying within the batch of aligned reads one or more abnormally aligned reads; and d) using the one or more abnormally aligned reads to identify a novel structural variant.

In some embodiments, the method further comprises counting a number of reads in the batch of aligned reads that align to alternate paths in the graph reference, and using the number of reads to identify known variants. In some embodiments, the method further comprises conducting steps a) through d) for at least one additional batch. In some embodiments, the method further comprises conducting steps a) through d) for at least one additional batch. In some embodiments, the known variants are previously documented for a target application. In some embodiments, the novel structural variant is not previously documented for a target application. In some embodiments, the known variants are variants that are present in the graph reference. In some embodiments, the novel structural variant is a variant not present in the graph reference. In some embodiments, a subset of the abnormally aligned reads from the batch is written out to a file and subsequently used to identify the novel structural variant. In some embodiments, a subset of the abnormally aligned reads from the batch is passed to a computer program to identify the novel structural variant without writing the subset of reads to a file. In some embodiments, abnormal alignment comprises one or more of the following: a) an aligned read pair orientation different from that of a majority of aligned read pairs; b) an aligned read pair insert length that is significantly smaller or larger than that of a majority of aligned read pairs; c) a read pair in which one read is aligned and one read is unaligned; d) a read in which a part of the read is clipped; e) a read pair in which an insert length is larger than the $99^{th}$, $98^{th}$, $97^{th}$, $95^{th}$ or $90^{th}$ percentile or smaller than the $1^{st}$, $2^{nd}$, $3^{rd}$, $5^{th}$, or $10^{th}$ percentile of insert lengths of a subset of aligned read pairs; and f) a read pair in which reads align to different reference sequences. In some embodiments the different reference sequences are from different chromosomes. In some embodiments, the method further comprises tracking additional features of reads that align to alternate paths in the graph reference using the additional features to identify known variants. In some embodiments, less than 1% of the plurality of sequence reads is read from a file more than one time. In some embodiments, less than 5% of the plurality of sequence reads is read from a file more than one time. In some embodiments, less than 10% of the plurality of sequence reads is read from a file more than one time. In some embodiments, less than 15% of the plurality of sequence reads is read from a file more than one time. In some embodiments, the known variants or the novel structural variant comprise an intra-species variant. In some embodiments, the known variants or the novel structural variant comprise an inter-species variant.

An aspect of the present disclosure provides a system to concisely characterize a graph reference alignment of a sequence read, in a format compatible with a format used for linear reference aligned reads, the system comprising: a) a receiving module configured to receive a graph alignment of a read to a graph reference sequence, wherein the graph reference sequence comprises known variants represented by variant paths relative to a reference sequence; b) a reporting module that characterizes the graph alignment of the read by reporting the start of its alignment relative to a coordinate of the reference sequence and, if the read aligns to a variant path, a read tag that represents an identification number of the variant path.

In some embodiments, the reporting module further reports a read flag that is set if the read aligns to a variant path. In some embodiments, if the read tag of b) is provided, the reporting module further outputs a second read tag that indicates the start of the aligned read relative to a coordinate of the variant path. In some embodiments, if the read tag of b) is provided, the reporting module further outputs a second read tag that indicates the start and end of the aligned read relative to a coordinate of the variant path. In some embodiments, if the read tag of b) is provided, the reporting module further outputs a second read tag that contains a string of alignment scores relative to the variant path. In some embodiments, the alignment scores include the number of matches, insertions or deletions. In some embodiments, if the read tag of b) is provided, the reporting module further outputs a second read tag that contains how many reads map to the variant path. In some embodiments, the reporting module further outputs a second read tag that contains how many reads map to the reference sequence. In some embodiments, the reporting module further outputs a second read tag that contains reads mapping to the reference sequence. In some embodiments, the reporting module further outputs a second read tag that indicates the read initially mapped to a variant path. In some embodiments, the start of the alignment indicates a projection onto the reference sequence.

An aspect of the present disclosure provides a system to determine an abnormal graph alignment of a sequence read pair, the system comprising a) a receiving module that receives a read pair aligned to a graph reference comprising a linear reference path, wherein at least one read of the read pair has some or all of its alignment on an alternate path; b) a translation module that translates the at least one read to the linear reference coordinate system and stores translational operation information as meta data; c) a computing module that takes as input the translated read, the meta data, and the second read in the read pair and computes properties specific to the read pair; and d) a decision module that takes the properties and classifies the pair as abnormally aligned to the graph reference or not.

In some embodiments, the properties comprise insert length relative to the linear reference path. In some embodiments, the properties comprise a CIGAR score relative to the linear reference path. In some embodiments, the properties comprise an alignment position relative to the linear reference path. In some embodiments, the alignment report is compatible with a downstream analysis tool. In some embodiments, the compatibility comprises being in a compatible file format. In some embodiments, the compatible file format is SAM. In some embodiments, the compatible file format is BAM. In some embodiments, the compatible file format is VCF.

An aspect of the present disclosure provides a method to generate a at least one phased alternate sequence path, the method comprising: a) obtaining a reference sequence; b) retrieving correlated loci on an alternative reference sequence; and c) generating at least one phased alternate sequence path comprising the correlated loci.

In some embodiments, the correlated loci are from two or more distinct origins. In some embodiments, the correlated loci comprise a set of different sequences which map to more than one location on the reference sequence. In some embodiments, at least two of the set of different sequences are phased. In some embodiments, the method further comprises indexing said phased set of different sequences.

An aspect of the present disclosure provides a method to index a reference sequence with alternate paths, the method comprising: (a) receiving a reference sequence; (b) receiving alternate sequences which map to the reference sequence; (c) generating k-mers of the reference sequence and the alternate sequences in less than or equal to two hours; and (d) indexing the reference sequence with alternate paths using said k-mers.

In some embodiments, the reference sequence is a nucleic acid sequence. In some embodiments, the nucleic acid sequence is a genomic sequence. In some embodiments, the nucleic acid sequence comprises double-stranded DNA, single-stranded DNA, DNA/RNA hybrids, single-stranded RNA, double stranded RNA, or complementary DNA (cDNA). In some embodiments, the nucleic acid sequence is a synthetic sequence. In some embodiments, the genomic sequence is from a human genome. In some embodiments, the genomic sequence is from a non-human genome. In some embodiments, the non-human genome is selected from the group consisting of a bacterial genome, a viral genome, a fungal genome, a protozoan genome, and a plant genome. In some embodiments, the reference sequence is an amino acid sequence In some embodiments, the amino acid sequence is a known sequence. In some embodiments, the amino acid sequence is a functional sequence. In some embodiments, the amino acid sequence is a synthetic sequence. In some embodiments, the amino acid sequence is human. In some embodiments, the amino acid sequence is non-human. In some embodiments, the non-human amino acid sequence is selected from the group consisting of a bacterial sequence, a viral sequence, a fungal sequence, a protozoan sequence, and a floral (plant) sequence. In some embodiments, the alternate path comprises an unknown amino acid sequence. In some embodiments, the generating uses a linear reference coordinate system to directly index the k-mers. In some embodiments, the generating does not involve assigning node IDs, edges, or paths.

An aspect of the present disclosure provides a method to index a reference sequence with alternate paths, the method comprising: (a) receiving a reference sequence; (b) receiving alternate sequences which map to the reference sequence; (c) generating an indexed plurality of k-mers of the reference sequence and the alternate sequences, wherein the indexed plurality of k-mers is less than or equal to 80 gigabytes in size; and (d) indexing the reference sequence with alternate paths using said k-mers.

In some embodiments, the computer space is selected from one or more of disk, ram, or address space. In some embodiments, the reference sequence is a nucleic acid sequence. In some embodiments, the nucleic acid sequence is a genomic sequence. In some embodiments, the nucleic acid sequence comprises double-stranded DNA, single-stranded DNA, DNA/RNA hybrids, single-stranded RNA, double stranded RNA, or complementary DNA (cDNA). In some embodiments, the nucleic acid sequence is a synthetic sequence. In some embodiments, the genomic sequence is from a human genome. In some embodiments, the genomic sequence is from a non-human genome. In some embodiments, the non-human genome is selected from the group consisting of a bacterial genome, a viral genome, a fungal genome, a protozoan genome, and a plant genome. In some embodiments, the reference sequence is an amino acid sequence. In some embodiments, the amino acid sequence is a known sequence. In some embodiments, the amino acid sequence is a functional sequence. In some embodiments, the amino acid sequence is a synthetic sequence. In some embodiments, the amino acid sequence is human. In some embodiments, the amino acid sequence is non-human. In some embodiments, the non-human amino acid sequence is selected from the group consisting of a bacterial sequence, a viral sequence, a fungal sequence, a protozoan sequence, and a floral (plant) sequence. In some embodiments, the generating step is performed by directly using a linear reference coordinate system and directly indexing the k-mers of alternate sequences as they appear in the linear coordinate system. In some embodiments, the generating does not involve assigning node IDs, edges, or paths.

An aspect of the present disclosure provides a method to query an index of k-mers in a reference sequence with alternate paths, the method comprising: (a) retrieving an index comprising a plurality of k-mers from a reference sequence with alternate paths; and (b) querying the index with k-mers at a rate of greater than or equal to 69,000 k-mers per second per compute thread.

In some embodiments, the querying is performed on multiple compute threads at a rate of greater than or equal to 345,000 k-mers per second per compute thread. In some embodiments, the number of compute threads is greater than 4. In some embodiments, the querying is performed on multiple compute cores at a rate of greater than or equal to 355,000 k-mers per second per core. In some embodiments, greater than 95% of processor work is dedicated to querying the index. In some embodiments, processor work is work solely dedicated to querying the index. In some embodiments, the processor work does not comprise one or more tasks selected from the group consisting of kernel tasks, memory swaps, or I/O. In some embodiments, the k-mers are a length of at least 20. In some embodiments, the k-mers are a length of at least 32.

An aspect of the present disclosure provides a method to compare sequences, the method comprising: (a) retrieving a read from a sequencer while the sequencer is conducting a sequencing assay; (b) comparing the read to a sequence while the sequencer is conducting the sequencing assay; and (c) determining if a specific locus is in the read.

In some embodiments, the method further comprises accumulating a count of occurrences of the specific locus.

An aspect of the present disclosure provides a method for phasing loci in a reference sequence that has alternate sequences, the method comprising: (a) retrieving a number of occurrences of multiple alternative paths in a sequence, wherein each multiple alternative path comprises loci; (b) grouping loci from different alternate paths into common groupings based on the number of occurrences for the multiple alternative paths; and (c) phasing the loci based upon common groupings.

An aspect of the present disclosure provides a method to compare sequences, the method comprising: (a) retrieving a read from a sequencer while the sequencer is conducting a sequencing assay; (b) encrypting the read while the sequencer is conducting the sequencing assay; and (c) comparing the read to a reference sequence without decrypting the read.

In some embodiments, the reference sequence is a sequence variation map. In some embodiments, the reference sequence is a reference nucleic acid sequence. In some embodiments, the nucleic acid sequence is a genomic sequence. In some embodiments, the nucleic acid sequence comprises double-stranded DNA, single-stranded DNA, DNA/RNA hybrids, single-stranded RNA, double stranded RNA, or complementary DNA (cDNA). In some embodiments, the nucleic acid sequence is a synthetic sequence. In some embodiments, the genomic sequence is from a human genome. In some embodiments, the genomic sequence is from a non-human genome. In some embodiments, the non-human genome is selected from the group consisting of a bacterial genome, a viral genome, a fungal genome, a protozoan genome, and a plant genome. In some embodiments, the reference sequence is an amino acid sequence. In some embodiments, the amino acid sequence is a known sequence. In some embodiments, the amino acid sequence is a functional sequence. In some embodiments, the amino acid sequence is a synthetic sequence. In some embodiments, the amino acid sequence is human. In some embodiments, the amino acid sequence is non-human. In some embodiments, the non-human amino acid sequence is selected from the group consisting of a bacterial sequence, a viral sequence, a fungal sequence, a protozoan sequence, and a floral sequence.

An aspect of the present disclosure provides a method to compare sequences, the method comprising: (a) retrieving a read from a sequencer while the sequencer is conducting a sequencing assay; (b) encrypting the read while the sequencer is conducting the sequencing assay; and (c) transmitting the encrypted read to a processing device.

In some embodiments, the method further comprises decrypting the encrypted read. In some embodiments, the method further comprises comparing the read to a reference sequence while the sequencing assay is in progress. In some embodiments, the method further comprises transmitting a decrypting key related to the encrypted read.

An aspect of the present disclosure provides a method to compare sequences, the method comprising: (a) retrieving a read from a sequencer while the sequencer is conducting a sequencing assay; (b) compressing the read on a processing device while the sequencer is conducting the sequencing assay; (c) decompressing the read while the sequencer is conducting the sequencing assay; and (d) comparing the read to a reference sequence while the sequencer is conducting the sequencing assay.

An aspect of the present disclosure provides a method for calling known variants, the method comprising: (a) retrieving a read; (b) generating a k-mer profile from the read; and (c) querying the k-mer profile to an index of k-mer profiles from a reference sequence with alternate paths to call known variants.

In some embodiments, the known variants are called using at least a single core at a rate greater than or equal to 10 variant calls per second per core.

An aspect of the present disclosure provides a system for compression of sequencing data, the system comprising: (a) a receiving module for receiving sequencing data; (b) a memory unit for storing the sequencing data; and (c) an encoding module having access to the memory and the sequencing data stored thereon, and configured to save some or all of the sequencing data.

In some embodiments, the sequencing data is compressed to a level equal or greater than 90% of the received sequencing data. In some embodiments, the sequencing data comprises fields selected from one or more of a sequence identifier, base call data, a comments line, and quality values for the base call data. In some embodiments, the sequencing data comprises amino acid call data. In some embodiments, the encoding module separates base call data in the sequencing data from the rest of the sequencing data. In some embodiments, the encoding module separates amino acid call data in the sequencing data from the rest of the sequencing data. In some embodiments, a nucleotide base in the base call data is associated with a nucleotide base selected from the group consisting of adenine, thymine, guanine, cytosine, and a base which was not determined. In some embodiments, an amino acid in the amino acid call data is associated with an amino acid selected from the group consisting of alanine (ala, A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), valine (val, V), and an amino acid which was not determined. In some embodiments, for an undetermined base the encoding module does not separate base call data in the sequencing data from the rest of the sequencing data to encode a read associated with the undetermined base. In some embodiments, the read associated with the undetermined base is compressed as an unseparated read. In some embodiments, the location of a read with an undetermined base is saved. In some embodiments, all reads with undetermined bases are saved. In some embodiments, the read associated with the undetermined base is smaller than 256 bases in length and a location of the undetermined base is saved in less than 1 byte. In some embodiments, the read associated with the undetermined base is less than 65536 bases in length and a location of the undetermined base is saved in less than 2 bytes. In some embodiments, the encoding module saves information using delta encoding. In some embodiments, the encoding module performs base-4 encoding on the nucleotide-based data. In some embodiments, the encoding module performs encoding on the amino acid-based data using a compressed alphabet that relates amino acids by chemical properties. In some embodiments, each field of the sequencing data is saved sequentially. In some embodiments, at least two fields are saved in a separate file. In some embodiments, at least two different files are saved using different compression algorithms performed on each field. In some embodiments, data in a sequence identifier field is compressed using delta encoding. In some embodiments, base call data is processed using a Burrows-Wheeler Transform. In some embodiments, the processing of the base call data further comprises running run-length encoding and compressing using Huffman Encoding. In some embodiments, a line for comments is compressed using delta encoding. In some embodiments, an additional line for comments is ignored when the field is empty. In some embodiments, quality value data is processed using a Burrows-Wheeler Transform. In some embodiments, the processing further comprises running run-length encoding and compressing using Huffman Encoding.

A system for compression of sequence alignment map (SAM) data, the system comprising: (a) memory having stored thereon the SAM data; (b) an encoding module having access to the memory and to the SAM data stored thereon, and configured to compress the SAM data to a level equal or greater than 80%.

In some embodiments, the encoding module compresses a query template name in the SAM data using delta encoding. In some embodiments, the encoding module compresses a reference sequence name in the SAM data using delta encoding. In some embodiments, the encoding module compresses a leftmost mapping position in the SAM data using delta encoding. In some embodiments, the encoding module compresses a reference name of a mate read in the SAM data using delta encoding. In some embodiments, the encoding module compresses a position of a mate read in the SAM data using delta encoding. In some embodiments, the encoding module compresses data from a CIGAR string using a Huffman coding method. In some embodiments, the encoding module compresses data from a CIGAR string using a dictionary-based method. In some embodiments, the encoding module compresses base call data from the SAM data using base 4 encoding. In some embodiments, the encoding module compresses quality data from the SAM data. In some embodiments, (a) the encoding module is configured to compress, using delta encoding, data from the SAM data comprising one or more of a query template name, a reference sequence name, a leftmost mapping position, a reference name of the mate read, and a position of the mate read; (b) the encoding module is configured to compress, using Huffman coding or a dictionary-based method, data from the SAM data comprising a CIGAR string; (c) the encoding module is configured to compress, using base-4 encoding, data from the SAM data comprising base call data; and (d) the encoding module is configured to compress data from the SAM data comprising quality data. In some embodiments, the SAM data is sequentially ordered.

An aspect of the present disclosure provides a system for compression of VCF data, the system comprising: a memory having stored thereon the VCF data; and an encoding module having access to the memory and to the VCF data stored thereon, and configured to encode the genomic data to a level equal or greater than 95% of the VCF data.

In some embodiments, the encoding module compresses a query template name in the VCF data using delta encoding. In some embodiments, the encoding module compresses a reference sequence name in the VCF data using delta encoding. In some embodiments, the encoding module compresses a leftmost mapping position in the VCF data using delta encoding. In some embodiments, the encoding module compresses a reference name of a mate read in the VCF data using delta encoding. In some embodiments, the encoding module compresses a position of a mate read in the VCF data using delta encoding. In some embodiments, the encoding module compresses data form a cigar string using Huffman coding method. In some embodiments, the encoding module compresses data form a cigar string using a dictionary-based method. In some embodiments, the encoding module compresses base call data from the VCF data using base 4 encoding. In some embodiments, the encoding module compresses quality data from the VCF data. In some embodiments, for a read an undetermined base call, the position of the undetermined base call is saved. In some embodiments, for all reads with undetermined base calls, the positions of the undetermined base calls are saved.

An aspect of the present disclosure provides a method for aligning raw proteomic sequence data, the method comprising: (a) retrieving raw proteomic sequence data; (b) mapping said raw proteomic sequence data to a location on a variation map, wherein the variation map comprises alternate paths; and (c) aligning the raw proteomic sequence data according to its location on the variation map.

In some embodiments, the mapping is performed by graph alignment. In some embodiments, the graph alignment uses at least one graph. In some embodiments, the mapping is performed using a gapped alignment. In some embodiments, the mapping is performed using a semi-gapped alignment. In some embodiments, the method further comprises accumulating a number of times a particular path from the alternative paths is mapped to in the mapping step.

An aspect of the present disclosure provides a method to generate at least alternate sequence path, the method comprising: a) obtaining a reference sequence; b) retrieving correlated loci on a reference sequence that are alternate to the reference sequence, and c) generating at least one alternate sequence path comprising the correlated loci.

In some embodiments, the correlated loci are from two or more distinct origins. In some embodiments, the correlated loci are a set of different sequences which map to more than one location on the reference sequence.

An aspect of the present disclosure provides a method to compare an amino acid sequence, the method comprising: a) retrieving an amino acid sequence; b) generating a k-mer profile from the amino acid sequence; and c) querying the k-mer profile to an index of k-mer profiles from a plurality of sequences within a database.

An aspect of the present disclosure provides a system for calling known variants to amino acid sequences, the system comprising: (a) retrieving an amino acid sequence; (b) generating a k-mer profile from the amino acid sequence; and (c) querying the k-mer profile to an index of k-mer profiles from a dataset of known amino acid and polymer sequences with alternate paths to call variants.

In some embodiments, known variants are identified using at least a single core at a rate greater than or equal to 10 variant calls per second per core.

An aspect of the present disclosure provides a system for compression of amino acid sequence data, the system comprising: (a) a module for receiving amino acid sequence data; (b) a memory unit for storing the amino acid sequence data; and (c) an encoding module having access to the memory and to the amino acid sequence data stored thereon, and configured to encode some or all of the amino acid sequence data.

An aspect of the present disclosure provides a method for identifying species and/or strains in a sample, the method comprising: a) retrieving a read; b) generating a k-mer profile from the read; c) querying the k-mer profile to an index of k-mer profiles from a reference sequence with alternate paths to call variants; and d) determining a species or a strain present in the sample based on the called variants.

In some embodiments, the k-mer profile includes gapped k-mers. In some embodiments, the k-mer profile condenses different sequences at a frequency of up to 1 in 1,000,000 bases. In some embodiments, an index of the alternate paths includes phased information In some embodiments, only k-mers directly associated with differences between strains are used. In some embodiments, the size of the k-mer index is reduced by at least 99% compared to the index of k-mer profiles from the reference sequence. In some embodiments, the size of the k-mer index is reduced by at least 99.9% compared to the index of k-mer profiles from the reference sequence. In some embodiments, only k-mer determinations directly associated with differences between strains are used for variant determination. In some embodiments, the size of the k-mer index is reduced by at least 99% compared to the index of k-mer profiles from the reference sequence. In some embodiments, wherein the size of the k-mer index is reduced by at least 99.9% compared to the index of k-mer profiles from the reference sequence.

BRIEF DESCRIPTION OF THE FIGURES

FIG. 5 shows an example of a reference sequence and alternate paths.

FIG. 8A and FIG. 8B show exemplary schematics illustrating offset normalization to reduce the number of CALs.

DETAILED DESCRIPTION

Definitions

Figure 1:
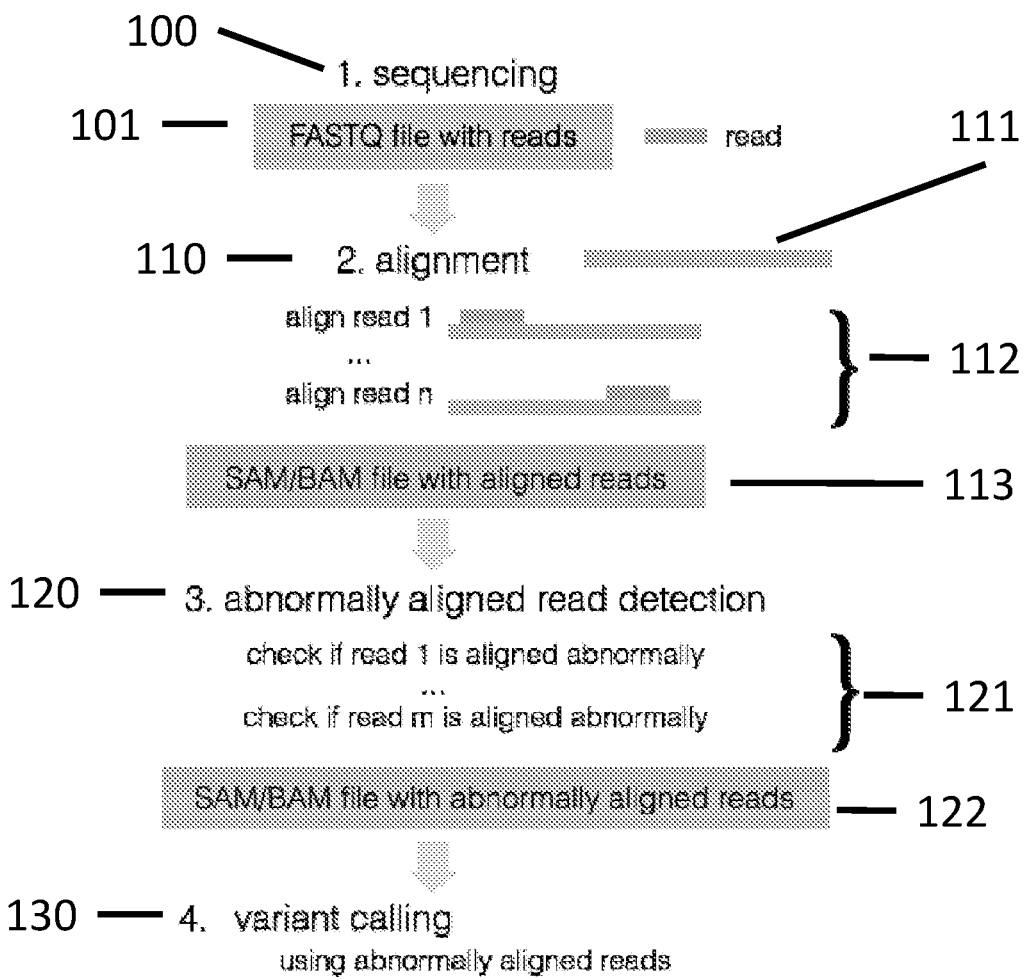
FIG. 1 shows an exemplary sequential model for genomic analysis.

The below terms are discussed below to illustrate meanings of the terms as used in this specification, in addition to the understanding of these terms by of those of skill in the art. As used in the specification and claims, the singular forms "a", "an" and "the" can include plural references unless the context clearly dictates otherwise. For example, the term "a cell" can include a plurality of cells, including mixtures thereof.

As used herein, the term "alignment" can be any computational process in which every sequence strings produced by a sequencer is matched to a reference string. An alignment can be, for example, a Smith Waterman local alignment, a gapped alignment or semi-gapped alignment.

Variability in the genome can be represented as "alternative paths." For example, a primary genome can be a linear sequence of DNA bases (represented by the letters A, C, T, and G). A secondary genome may have a different sequence of DNA bases which represents the biological diversity between the primary and secondary subject.

A "graph reference" represents a condensed representation of one or more sequences, in which sequence intervals that are shared by all sequences are collapsed to one sequence path and sequence intervals that are different are kept as alternate paths.

A "linear reference" can be a representation of a sequence in which no more than one option is specified for the identity of each element. In some specifications, the sequence are nucleic acids, in other they are proteins.

"Correlated loci" can mean sequences from two genomes, or a subject genome and a reference genome, which generally represent the same genomic region. It can also mean sequences from one genome but two or more different regions. Generally correlated loci will be within the same species. They generally will also be within the same subject. Correlated loci can be correlated via linkage disequilibrium, conserved regions on a haploid, a priori data such as 1000 genomes or the like.

Genomic information can be "phased." Phased sequences capture unique chromosomal content, including mutations that may differ across chromosome copies. Phased sequencing can, in some instances, distinguish between maternally and paternally inherited alleles.

The term "k-mer" can refers to all the possible subsequences of length k that are contained in a sequence.

A "genome variation map", can be constructed where individual subject genomes which go into the construction of the map will be merged into the reference genome at the points where it matches the primary sequence, with variations appearing as additional alternate paths along the genome. The resulting map will include multiple forms of genomic variation. A genome variation map can be represented as a graph.

The term "assembly" can be any computational process in which sequence strings produced by a sequencer are merged between one another with the objective to reconstruct the original sequence string, from which the set of all sequence strings were derived.

The term "remote alignment" can be any computational process by which the alignment is divided into a certain predefined number of independent subtasks and for which subtasks can be performed by an independent computer device capable of receiving the sequence strings, of aligning the sequence strings and of transmitting the sequence strings to the appropriate computational device of providing the final whole and complete alignment of all the subtasks.

The term "index" can by any database that is used to optimize the access of data. The database can consist of keys. These keys can be attributes on which the search on the original database is going to be based. An index of a genome variation map or sequence graph can contain a database of the short sequences (k-mers) that are contained in the sequence graph along with their offset in the sequence graph and alternate path they belong to in the sequence graph. An index of a genome variation map, or sequence graph, can also be a database comprised of a Burrows-Wheeler transform (BWT) on the sequence graph, which can use positional markers to annotate locations of alternate paths within the transformed sequence. This latter index can be stored using wavelet trees, known to those skilled in the art. In other cases, the index does not comprise a BWT with positional markers using wavelet trees for encoding.

The term "hash table" can describe a method or structure that can allow for accelerated searching within the index.

The term "reference sequence" can refer to a sequence string composed of the information required to define the molecule at hand. For example, a whole human genome would be a sequence string of nucleotides consisting of about 3 billion bases to be compliant for the definition of a human genome. A reference genome (alternately a reference assembly) can be a reference sequence. A reference genome can be a digital nucleic acid sequence database, assembled by as a representative example of a set of related nucleic acids. A reference genome can be, for example, an example of a particular species' genome. In some instances, a reference genome can comprise alternative paths.

The term "metadata" describes the composition of different of types structures added in an ordered manner that can be consistent.

"Raw genetic sequence data" is data obtained from sequencing reactions. Raw genetic sequence data can be text-based, for example it can have a FASTA format. A FASTA format is a text-based format for representing either nucleotide sequences or peptide sequences, in which nucleotides or amino acids are represented using single-letter codes. Raw genetic sequence data can be text-based format for storing both a biological sequence (e.g., base call data or amino acid call data) and its corresponding quality scores and any other associated data or metadata. For example, it can have a FASTQ format. FASTQ format is a text-based format for storing both a biological sequence and its corresponding quality scores. In some instances, the sequence letter and quality score are each encoded with a single ASCII character for brevity. In some instances, raw genetic sequence data can be converted from one format to another using a format converter. In some instances, raw genetic sequence data is called a "read."

A "sequencing device" is a device that performs a sequencing reaction. Sequencing devices can be used to generate raw genetic sequence data. In some instances, the methods described herein can be performed while the sequencing device is performing the sequencing reaction. For example, as sequence data is generated by the sequencing device those data can be encrypted and aligned while encrypted. In some instances, a sequencing device can output SAM data.

A "read pair" can mean a pair of sequenced reads that originate from a connected nucleic acid sequence of which at least two regions are sequenced. The sequence of the nucleotide string in between the sequenced reads, in some instances, not known. In some read pair generation techniques, the length of the total nucleotide string does not vary much. The distribution on the length of the whole nucleotide string (that is, the insert length) can, in some instances, be estimated when the sequenced reads are aligned to a reference sequence that is similar to the sample. This information can be used for structural variant calling: read pairs that align with an insert length that has very low probability in this distribution, indicate that there may be a structural variant present in the sample. In addition, for some read pair generation techniques, the two sequenced reads of the pair are most likely to align to a reference sequence with a particular orientation, e.g. the leftmost read aligns to the reference sequence as-is (forward' orientation), while the rightmost read aligns to the complement of the reference sequence (reverse' orientation). Deviations from the most likely orientation in an aligned read pair can be an indication for structural variation.

The length of the insert length in a read pair can vary depending on the particular sequencing technology utilized. NGS platforms can provide read pairs, of which the insert length can vary in size from hundreds to thousands or tens of thousands of base pairs. In some specifications, the insert length distribution follows a specific model.

In some specifications the "target application" can refer to a human population for which the graph reference represents variation. In other cases, the "target application" can refer to one or more populations of interest, such as a species, a specific disease population, a geographic population, a plant population, a fungal, bacterial or viral strain or set of strains or combinations thereof. The target application can also involve the diploid or multiploid character of one or more individuals or species.

The SAM Format (or "SAM data") is a text format for storing sequence data in a series of tab delimited ASCII columns. SAM data can be generated as a human readable version of its sister BAM Format ("BAM data"), which stores the same data in a compressed, indexed, binary form. SAM format data can be output from aligners that read FASTQ files and assign the sequences to a position with respect to a known reference genome. SAM can also be used to archive unaligned sequence data generated directly from sequencing machines. In some instances, SAM data comprises CIGAR strings. The CIGAR string is a sequence of base lengths and the associated operation. They are used to indicate properties, for example which bases align (either a match/mismatch) with the reference, are deleted from the reference, or are insertions that are not in the reference.

The Variant Call Format (VCF) specifies the format of a text file used for storing sequence variations in the interdisciplinary field of bioinformatics. "VCF data" is data stored in the VCF format. The variant call format stores only the variations needed to be stored along with a reference sequence.

The General feature format (GFF) stored all of the genetic data, much of which is redundant because it will be shared across the genomes. "GFF data" is data stored in the GFF format.

A "graph alignment" can include the analysis of genomic data using graphs and graph representations. For example, a genome variation map graph can be used to analyze raw sequence data by graph alignment.

The term "subject", as used herein, generally refers to a biological entity containing expressed genetic materials. The biological entity can be a plant, animal, or microorganism, including, e.g., bacteria, viruses, fungi, and protozoa. The subject can be tissues, cells and their progeny of a biological entity obtained in vivo or cultured in vitro. The subject can be a mammal. The mammal can be a human.

A "sample" or "nucleic acid sample" can refer to any substance containing or presumed to contain nucleic acid. The sample can be a biological sample obtained from a subject. The nucleic acids can be RNA, DNA, e.g., genomic DNA, mitochondrial DNA, viral DNA, synthetic DNA, or cDNA reverse transcribed from RNA. The nucleic acids in a nucleic acid sample generally serve as templates for extension of a hybridized primer. In some embodiments, the biological sample is a liquid sample. The liquid sample can be whole blood, plasma, sputum, joint fluid, serum, ascites, cerebrospinal fluid, sweat, urine, tears, saliva, buccal sample, cavity rinse, or organ rinse. The liquid sample can be an essentially cell-free liquid sample (e.g., plasma, serum, sweat, urine, tears). In other embodiments, the biological sample is a solid biological sample, e.g., feces or tissue biopsy, e.g., a tumor biopsy. A sample can also comprise in vitro cell culture constituents (including but not limited to conditioned medium resulting from the growth of cells in cell culture medium, recombinant cells and cell components).

"Nucleotides" can be biological molecules that can form nucleic acids. Nucleotides can have moieties that contain not only the known purine and pyrimidine bases, but also other heterocyclic bases that have been modified. Such modifications include methylated purines or pyrimidines, acylated purines or pyrimidines, alkylated riboses, or other heterocycles. In addition, the term "nucleotide" includes those moieties that contain hapten, biotin, or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the like.

"Nucleotides" can also include locked nucleic acids (LNA) or bridged nucleic acids (BNA). BNA and LNA generally refer to modified ribonucleotides wherein the ribose moiety is modified with a bridge connecting the 2' oxygen and 4' carbon. Generally, the bridge "locks" the ribose in the 3'-endo (North) conformation, which is often found in the A-form duplexes. The term "locked nucleic acid" (LNA) generally refers to a class of BNAs, where the ribose ring is "locked" with a methylene bridge connecting the 2'-O atom with the 4'-C atom. LNA nucleosides containing the six common nucleobases (T, C, G, A, U and mC) that appear in DNA and RNA are able to form base-pairs with their complementary nucleosides according to the standard Watson-Crick base pairing rules. Accordingly, BNA and LNA nucleotides can be mixed with DNA or RNA bases in an oligonucleotide whenever desired. The locked ribose conformation enhances base stacking and backbone pre-organization. Base stacking and backbone pre-organization can give rise to an increased thermal stability (e.g., increased Tm) and discriminative power of duplexes. LNA can discriminate single base mismatches under conditions not possible with other nucleic acids.

The terms "polynucleotides", "nucleic acid", "nucleotides", "sequence" and "oligonucleotides" can be used interchangeably. They can refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "variant" can be an alteration in the normal sequence of a nucleic acid sequence or an amino acid sequence (e.g., a gene or a gene product). In some instances, a genotype and corresponding phenotype is associated with a variant. In other instances, there is no known function of a variant. A variant can also mean a sequence difference relative to a reference sequence. A variant can be a SNP. A variant can be a SNV. A variant can be an insertion of a plurality of nucleotides. A variant can be a deletion of a plurality of nucleotides. A variant can be a mutation. A variant can be a copy number variation. A variant can be a structural variant. A variant can be nucleotide insertions or deletions that translate into a synonymous mutation. A variant can be nucleotide insertions or deletions that translate into non-synonymous mutation.

A "single nucleotide polymorphism (SNP)" can mean a variant that is one (1) base long.

An "indel" can mean a small variant of two or more bases long. An indel can be an insertion or a deletion. In some instances, an indel can be a small structural variant.

A "known variant" can mean a variant that has previously been reported. A known variant can be a variant that is included into the graph reference. In some specifications the known variant has been reported in external media such as databases, journals, medical records. In some specifications the reports can be considered internal.

A "novel variant" can be a variant in a sample that is not included in the graph reference. In some specifications a novel variant can be a variant previously reported but not included. In other specifications, a novel variant can be a hitherto unknown variant.

A "structural variant" can mean a longer variant usually considered 50 or more bases.

A "read cycle" can be a process of scanning through the bulk of a set of reads. A small fraction of reads may be discarded in a read cycle or be included more than once. In other read cycle different operation on the reads can be undertaken. For instance, these could include but are not limited to read quality recalibration, realignment, filtering, other statistical operations.

"Variant calling" can be defined as the process of determining if a variant is present in a sequence. Variants can include but are not limited to SNPs, indels, structural variants, and synonymous or non-synonymous inducing mutations.

The term "target polynucleotide," as use herein, generally refers to a polynucleotide of interest under study. In certain embodiments, a target polynucleotide contains one or more sequences that are of interest and under study. A target polynucleotide can comprise, for example, a genomic sequence. The target polynucleotide can comprise a target sequence whose presence, amount, and/or nucleotide sequence, or changes in these, are desired to be determined. In some instances, a target polynucleotide is aligned to an alternative path.

The term "genomic sequence", as used herein, can refer to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome. "Genomic sequence" can also be a sequence that occurs on the cytoplasm or in the mitochondria.

The terms "determining", "measuring", "evaluating", "assessing," "assaying," and "analyzing" can be used interchangeably herein to refer to any form of measurement, and include determining if an element is present or not. These terms can include both quantitative and/or qualitative determinations. Assessing may be relative or absolute. "Assessing the presence of can include determining the amount of something present, as well as determining whether it is present or absent.

The term "genomic fragment", as used herein, can refer to a region of a genome, e.g., an animal or plant genome such as the genome of a human, monkey, rat, fish or insect or plant. A genomic fragment may or may not be adaptor ligated. A genomic fragment may be adaptor ligated (in which case it has an adaptor ligated to one or both ends of the fragment, to at least the 5' end of a molecule), or non-adaptor ligated.

The term "sequencing", as used herein, can refer to a method by which the identity of at least 10 consecutive nucleotides (e.g., the identity of at least 20, at least 50, at least 100, at least 200, or at least 500 or more consecutive nucleotides) of a polynucleotide are obtained.

The term "barcode sequence" as used herein, generally refers to a unique sequence of nucleotides that can encode information about an assay. A barcode sequence can encode information relating to the identity of an interrogated allele, identity of a target polynucleotide or genomic locus, identity of a sample, a subject, or any combination thereof. A barcode sequence can be a portion of a primer, a reporter probe, or both. A barcode sequence may be at the 5'-end or 3'-end of an oligonucleotide, or may be located in any region of the oligonucleotide.

The term "mutation", as used herein, generally refers to a change of the nucleotide sequence of a genome or functional gene. Mutations can involve large sections of DNA (e.g., copy number variation). Mutations can involve whole chromosomes (e.g., aneuploidy). Mutations can involve small sections of DNA. Examples of mutations involving small sections of DNA include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus", as used herein, can refer to a location of a gene, nucleotide, or nucleotide sequence on a chromosome. An "allele" of a locus, as used herein, can refer to an alternative form of a nucleotide or sequence at the locus. A "wild-type allele" generally refers to an allele that has the highest frequency in a population of subjects. A "wild-type" allele generally is not associated with a disease. A "mutant allele" generally refers to an allele that has a lower frequency that a "wild-type allele" and may be associated with a disease. A "mutant allele" may not have to be associated with a disease. The term "interrogated allele" generally refers to the allele that an assay is designed to detect.

The term "single nucleotide polymorphism", or "SNP", as used herein, generally refers to a type of genomic sequence variation resulting from a single nucleotide substitution within a sequence. "SNP alleles" or "alleles of a SNP" generally refer to alternative forms of the SNP at particular locus. The term "interrogated SNP allele" generally refers to the SNP allele that an assay is designed to detect.

Sequence Alignment

Many next generation sequencing techniques generate short read sequences which can then be aligned and assembled into longer sequence information. Short read sequences can be difficult to align accurately when there are multiple good candidate alignment locations. Short read sequences can be difficult to align accurately when there are variations present in the sample. Herein provided are methods to address these problems. In these methods, the best alignment for a pair of reads can be found by taking into account the alignment qualities of the individual reads in the pair and features of the pair's alignment, such as the distance between the aligned reads in the pair and the relative orientation of the aligned reads in the pair. In some embodiments, the probability of observing these alignment features in a pair of reads can be estimated based on knowledge of the sequencing technology and the nature of the sample and used to score the pair's alignment.

For example, when using a typical paired-end sequencing library and a reference sequence similar to the sample sequence, the majority of read pairs will align with the same relative orientation in the reads that make up the pair, which can be called 'normal orientation'. Deviations from this normal orientation can be due to experimental errors or the presence of variation in the sample. The probability of a read pair aligning with any type of orientation different from normal orientation can be estimated based on the expected rate of variation in the sample (including different types of variations associated with different read pair orientations) and the expected experimental error rate. For each relative orientation of the reads in a read pair, the insert length distribution can also be estimated. The product of the read pair orientation probability and the insert length probability can be used to indicate how likely a possible read pair alignment is correct. This factor can be used to score the quality of possible alignments for a pair of reads, in addition to the alignment qualities of the individual reads in a pair.

The alignment quality for a read or a pair of reads can also depend on the alignment features of other reads or pairs of reads, for example, other reads or read pairs with the same barcode. In this manner, prior knowledge about the origin of reads or read pairs with the same barcode can be used to identify the alignment that is most likely to be correct.

The alignment qualities of reads in a subset of reads can be based on the alignment qualities of the individual reads and on an estimated probability of observing the alignment features of other reads in the subset. For example, the reads in the subset can be reads with the same barcode.

Variants (e.g., genomic variants) are differences in a sequence (e.g., a nucleic acid sequence) relative to a similar reference sequence. Structural variants (SVs) are variants that are large relative to the usual short-read sequence length—for example, for nucleic acid sequences structural variants are usually considered to be variants larger than 50 bp—and can therefore be difficult to detect with short read technology. The graph reference alignment methods disclosed herein can make it possible to include variants as prior knowledge when aligning so that these variants can be detected with better sensitivity, specificity and speed. Structural variants can also be included into the graph reference and detected by aligning reads to them.

The number of variants included in a graph reference can in practice be limited by memory constraints or efficiency considerations. Because of this, variants present in a sample may not be included in the graph reference and there is a need to detect them as 'novel' variants. Novel structural variants can be especially hard to detect due to their large size relative to the typical short read length. Disclosed herein are methods to detect novel variants within a graph reference paradigm. The method can comprise (a) obtaining a plurality of sequences, (b) aligning the plurality of sequences against a graph reference, and (c) using a plurality of sequences which align abnormally to identify novel variants.

In order to detect novel structural variants, one can 1) obtain sequence reads; 2) align them and write them to a file; 3) scan the file of aligned reads for reads that indicate structural variation; and 4) detect structural variants based on these reads. This procedure is depicted, for example, in FIG. 1. In this example, the sequences are read data contained in a FASTQ file 101 obtained from sequencing 100. Alignment 110 of these reads takes place with respect to a reference sequence 111. The first read cycle 112 involves processing the reads via alignment.

The product is a SAM or BAM file with the aligned reads 113. The file can contain the same number or a different number of reads than those analyzed in the first read cycle. Abnormally aligned read detection 120 is conducted in the second read cycle 121 which involves scanning through the SAM or BAM file with aligned reads to detect abnormally aligned reads. The abnormally aligned reads can be saved in a separate SAM or BAM file 122. Variants and/or structural variants can then be detected 130 based on these abnormally aligned reads.

The fraction of reads that indicate the presence of structural variation can be smaller than 5%, or even 1%. Scanning through all the aligned reads to collect this fraction of reads can be inefficient—this step can often be the most time-consuming step in structural variation detection. Disclosed herein are methods to detect novel variants efficiently in a graph reference paradigm. The method can comprise: a) obtaining a plurality of sequence reads; b) creating a batch of aligned reads by a process comprising aligning a subset of the plurality of sequence reads against a graph reference, wherein the graph reference comprises known variants represented by alternate paths; and c) identifying within the batch of aligned reads one or more abnormally aligned reads and using the one or more abnormally aligned reads to identify an unknown structural variant. In some embodiments, the method is carried out for n batches of reads.

Figure 2:
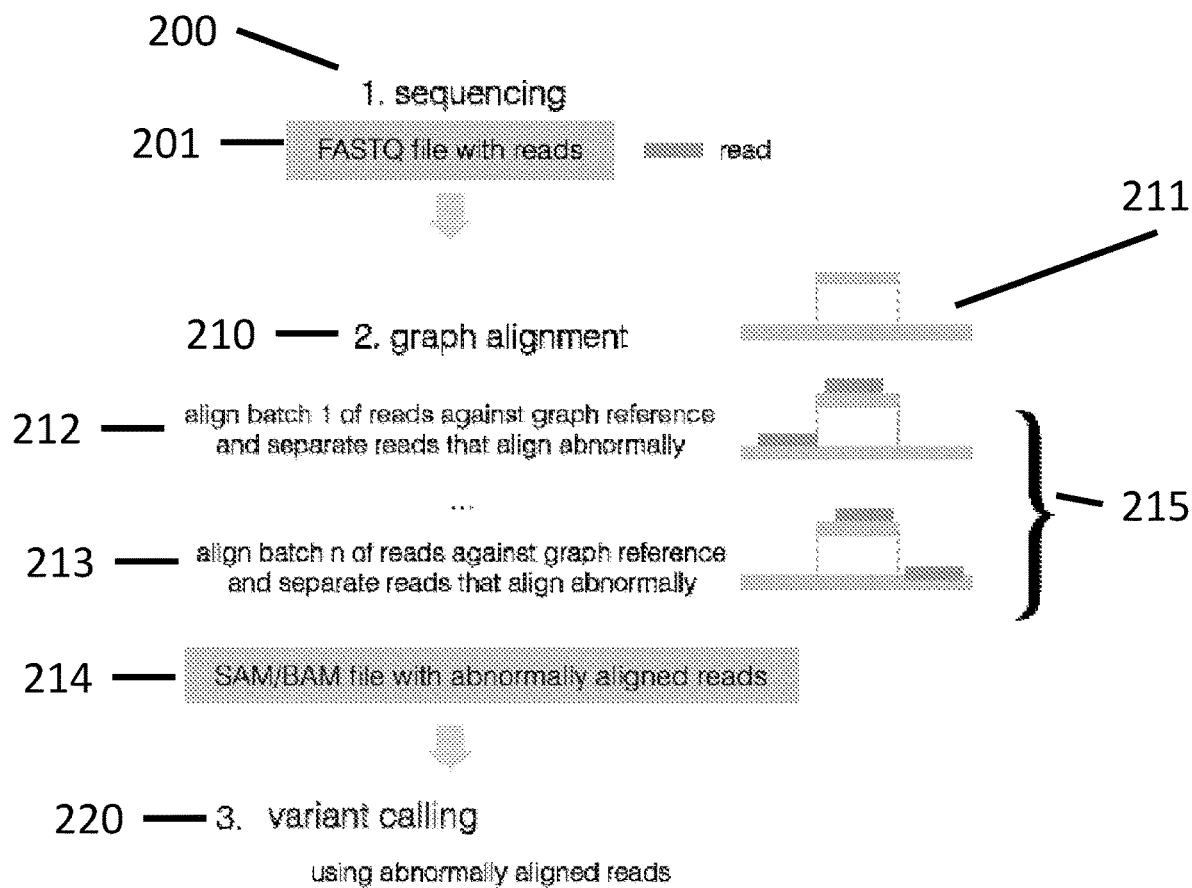
FIG. 2 shows an exemplary streaming model for genomic analysis.

FIG. 2 depicts an example of a procedure to detect novel variants efficiently in a graph alignment paradigm. Sequencing 200 produces sequence read data (e.g., in a FASTQ file) 201. The reads are aligned 210 using a graph reference 211 in batches of one or more reads 212 213. The number of reads in a batch can be small compared to the total number of sequencing reads in a sample. As the reads in the batch are aligned, those that align abnormally are identified and separated. They can be written to a SAM or BAM file 214. In this manner, the alignment and variant detection can be performed without the need to scan through all aligned reads to identify abnormally aligned reads. Reads can be marked as abnormally aligned at alignment time, so there is only one read cycle 215 over the large number of reads, without need for a second read cycle. Abnormally aligned reads can be used for calling variants (including structural variants) 220.

In some cases, the abnormally aligned reads from different batches are used to identify novel structural variants. In some cases, abnormally aligned reads from the same batch are used to identify novel structural variants. In some cases, a subset of the abnormally aligned reads from one or more batches is used to identify novel structural variants, for example after being written out to a file. In some cases, a subset of the abnormally aligned reads from one or more batches is passed to a computer program to identify novel structural variants without writing the reads to a file first.

In some cases, the known variants are variants that are previously documented. In some cases, the novel variants are variants that are not previously documented for the target application. In some cases, the known variants are variants that are included in the graph reference. In some cases, the novel variants are variants that are not included in the graph reference.

In some cases, in the batch of aligned reads, the number of reads aligned to alternate paths in the graph reference is counted and used to identify known variants.

In some cases, the variants represented by the alternate graphs in the graph reference can be structural variants. In some cases, the novel variants identified are structural variants.

In some cases, the alignment is performed using a gapped alignment. In some cases the alignment is performed using a semi-gapped alignment.

In some cases, the subset of the plurality of sequence reads used to identify novel structural variants includes reads that align abnormally to all alternate paths in the graph reference.

Abnormal alignment can involve aligning with a different pair orientation (that is, the orientation of the two aligned reads in the pair) than that of the majority of the aligned read pairs. Abnormal alignment can involve read pairs with an insert length significantly smaller or larger than the average or median insert length of the aligned read pairs. The abnormal insert length can be larger than the $99^{th}$, $90^{th}$, $95^{th}$, $97^{th}$, $98^{th}$, $97^{th}$, $96^{th}$, $95^{th}$, $94^{th}$, $93^{rd}$, $92^{nd}$, $91^{st}$, or $90^{th}$ percentile.

The abnormal insert length can be smaller than the $1^{st}$, $2^{nd}$, $3^{rd}$, $4^{th}$, $5^{th}$, $6^{th}$, $7^{th}$, $8^{th}$, $9^{th}$, or $10^{th}$ percentile of the insert length of a subset of aligned reads. The abnormal insert length can be set as larger or smaller than some user-specified value. In some cases, abnormal alignment involves one read being aligned while the other is unaligned. In some cases, abnormal alignment involves a fraction of the sequence being clipped. A clipped fraction means that this fraction of the sequence is not aligned. In some embodiments, the portion of the read that is clipped is at least 5%, 10%, 15%, 20%, 25%, 30%, 35%, 40%, 45%, or 50% of the read.

Figure 3:
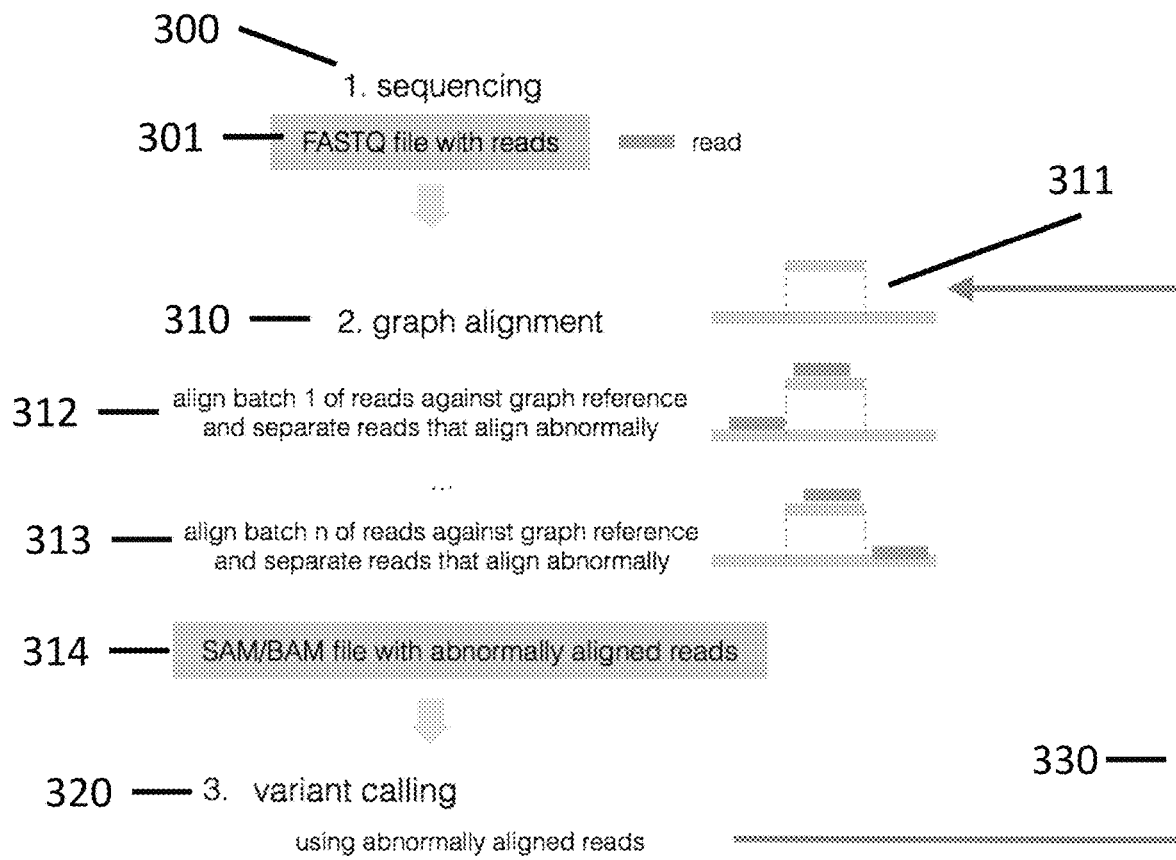
FIG. 3 shows an exemplary self-updating streaming model for genomic analysis.

As depicted for example in FIG. 3, in some cases a subset of the variants found can then be added automatically to the graph so that the graph becomes self-updating. In this example, the sequences are read data 301 (e.g., contained in a FASTQ file) obtained from sequencing 300. The sequence reads are aligned 310 using a graph reference 311 in batches of one or more reads 312 313. The batches can contain a small number of reads relative to the total number of reads in the FASTQ file. As the reads in the batch are aligned, those that align abnormally can be identified and separated. They can be written to a SAM or BAM file 314. In this manner, the alignment and identification of abnormally aligned reads are performed in just one read cycle. Novel variants and/or structural variants can then be detected 320 based on these abnormally aligned reads. A subset of the variants found can then be added to the graph in a self-updating fashion 330. Through this procedure, the graph alignment and variant detection method becomes self-improving upon subsequent analyses.

In some embodiments, variants need to satisfy certain conditions in order to be added to the graph, such as frequency in a sample set, length, type or quality conditions. Imposing such conditions can ensure that the graph reference remains concise and relevant for the application.

In some cases, the graph reference is used and progressively updated in more than one alignment and variant detection. It can be used and updated on the same computer or on multiple computers. In some cases, the graph reference is stored and updated in a central repository and shared among one or more computers.

Reads that are aligned using a graph reference can be written in a SAM format that is compatible with the SAM format for reads aligned against a linear reference. One or more different bit flags or read tags can be included to convey additional information. For example, a format to output reads that are aligned using a graph reference can include an optional bit flag that is set if the read alignment overlaps a variant, a read tag that characterizes the location of the alignment relative to the reference and/or variant path, and a read tag the indicates which variant the read aligns to. In some cases, the alignment of a read that aligns overlapping with an alternate path is translated back to the linear reference coordinates. An additional read tag can be used that shows the start of the aligned sequence relative to the coordinate of the variant path. An additional read tag can be used that indicates both the start and end of the aligned read relative to the coordinate of the variant path. An additional read tag can be used that contains alignment scores including, but not limited to, number of matches, mismatches, insertions, deletions, and start position related to the variant path. Such a read tag can also include alignment scores with respect to the reference path depending on the mapping. In some cases, the start of the alignment indicates a projection to the linear reference path. An additional read tag can be used detailing whether the read could have passed through the alternate path, but instead it mapped to the reference path. An additional read tag can be used detailing how many alternate paths the read passed through. An additional read tag can be used detailing how many alternate paths the read did not pass through, and instead mapped to the reference path. An additional read tag can be used detailing if a read starts mapping to a variant path.

Next Generation Sequencing Platforms

Sequencing information that is aligned, assembled, or otherwise processed using technique of the present disclosure can be from a next-generation sequencing (NGS) platform. The techniques of the present disclosure can be used with sequencing information of different source platforms, different file formats, different read lengths, different accuracies, different quality scores, different error rates, and different predominant types or sources of error.

The NGS platform can be a commercially available platform. Commercially available platforms can include but are not limited to platforms for sequencing-by-synthesis, ion semiconductor sequencing, pyrosequencing, reversible dye terminator sequencing, sequencing by ligation, single-molecule sequencing, sequencing by hybridization, and nanopore sequencing. Platforms for sequencing by synthesis are available from, for example, Illumina, 454 Life Sciences, Helicos Biosciences, and Qiagen. Illumina platforms can include, for example, Illumina's Solexa platform, Illumina's Genome Analyzer. Exemplary Illumina platforms are described in Gudmundsson et al (Nat. Genet. 2009 41:1122-6), Out et al (Hum. Mutat. 2009 30:1703-12) and Turner (Nat. Methods 2009 6:315-6), U.S. Patent Application Pub Nos. US20080160580 and US20080286795, and U.S. Pat. Nos. 6,306,597, 7,115,400, and 7,232,656. 454 Life Science platforms can include, for example, the GS Flex and GS Junior. Exemplary 454 Life Science platforms are described in U.S. Pat. No. 7,323,305. Platforms from Helicos Biosciences include the True Single Molecule Sequencing platform. Platforms for ion semiconductor sequencing include the Ion Torrent Personal Genome Machine (PGM) and are described, for example, in U.S. Pat. No. 7,948,015. Platforms for pryosequencing include the GS Flex 454 system and are described, for example, in U.S. Pat. Nos. 7,211,390, 7,244,559, and 7,264,929. Platforms and methods for sequencing by ligation include the SOLiD sequencing platform and are described, for example, in U.S. Pat. No. 5,750,341. Platforms for single-molecule sequencing include the SMRT system from Pacific Bioscience and the Helicos True
Single Molecule Sequencing platform.

While the automated Sanger method can be considered as a 'first generation' technology, Sanger sequencing including the automated Sanger sequencing can also be employed by the methods of the present disclosure. This technology can involve short segments of DNA of up to, but not limited to, about 1000 base pairs given the relative ease and accuracy of sequencing. Additional sequencing methods that comprise the use of developing nucleic acid imaging technologies, including but not limited to atomic force microscopy (AFM) or transmission electron microscopy (TEM), are also encompassed by the methods of the present disclosure. Exemplary sequencing technologies are further described below.

The next generation sequencing technology can utilize the Ion Torrent sequencing platform, which pairs semiconductor technology with a sequencing chemistry to directly translate chemically encoded information (A, C, G, T) into digital information (0, 1) on a semiconductor chip. Without wishing to be bound by theory, when a nucleotide is incorporated into a strand of DNA by a polymerase, a hydrogen ion is released as a byproduct. The Ion Torrent platform detects the release of the hydrogen atom as a change in pH. A detected change in pH can be used to indicate nucleotide incorporation. The Ion Torrent platform comprises a high-density array of micro-machined wells to perform this biochemical process in a massively parallel way. Each well holds a different library member, which may be clonally amplified. Beneath the wells is an ion-sensitive layer and beneath that an ion sensor. The platform sequentially floods the array with one nucleotide after another. When a nucleotide, for example a C, is added to a DNA template and is then incorporated into a strand of DNA, a hydrogen ion will be released. The charge from that ion will change the pH of the solution, which can be identified by Ion Torrent's ion sensor. If the nucleotide is not incorporated, no voltage change will be recorded and no base will be called. If there are two identical bases on the DNA strand, the voltage will be double, and the chip will record two identical bases called. Direct identification allows recordation of nucleotide incorporation in seconds. Library preparation for the Ion Torrent platform generally involves ligation of two distinct adaptors at both ends of a DNA fragment. These libraries can involve a separate emulsion PCR to amplify the sequences prior to any sequencing, which can complicate and slow down the process. Additionally, this two-step process can yield a higher error rate (e.g., 0.5-2.5%; indel error rate of 1.5 per 100 base pairs), especially for homopolymers, compared to other next generation sequencing platforms. Moreover, complicated regions comprised of AT-rich and GC-rich segments can yield a low coverage. For example, the preparation and sequencing times for an Ion Torrent PGM sequencer with an Ion 318™ Chip v2 can be up to 8 hours and 4-7 hours, respectively. Based on the previous setup, the system can output anywhere from 600 megabytes to 2 gigabytes of data per run, comprised of 200 or 400 base pair single nucleotide sequences. The phred quality score (Q) for each read can range from 10 to 30, which translates to a sequencing accuracy of 90% to 99.9%, respectively.

The next generation sequencing technology can utilize an Illumina sequencing platform, which generally employs cluster amplification of library members onto a flow cell and a sequencing-by-synthesis approach. Cluster-amplified library members are subjected to repeated cycles of polymerase-directed single base extension. Single-base extension can involve incorporation of reversible-terminator dNTPs, each dNTP labeled with a different removable fluorophore. The reversible-terminator dNTPs are generally 3' modified to prevent further extension by the polymerase. After incorporation, the incorporated nucleotide can be identified by fluorescence imaging. Following fluorescence imaging, the fluorophore can be removed and the 3' modification can be removed resulting in a 3' hydroxyl group, thereby allowing another cycle of single base extension. Library preparation for the Illumina platform generally involves ligation of two distinct adaptors at both ends of a DNA fragment. These ligated DNA fragments can vary in length up to, but not limited to, 300 base pairs depending on the desired output read-size (commonly referred as short reads). Recent library preparations such as the TruSeq long read technology can allow synthesized reads of up to 10 kilobases; however, these can be limited to the HiSeq platform versions. Library preparations can involve single or pair-end reads. Some examples of pair-end preparations are 2×300 base pair, 2×250 base pair, or 2×150 base pair nucleotide sequences. The average preparation time involves approximately 8 hours. Some popular and commercially available systems include the MiSeq, NextSeq 500 and HiSeq 2500, and have variable data output size and sequencing time. A MiSeq sequencing run can take up to 60 hours and can output approximately 13 to 16 gigabytes per run, while the NextSeq 500 and HiSeq 2500 can take up to 30 hours and 60 hours and can output 100 to 120 gigabytes and 250 to 300 gigabytes per run, respectively. Noticeably, the sequencing error rates for all systems can be about 0.1% with a high accuracy of 99.9% (phred quality score (Q) of 30).

The next generation sequencing technology can be the Helicos True Single Molecule Sequencing (tSMS), which can employ sequencing-by-synthesis technology. In the tSMS technique, a polyA adaptor can be ligated to the 3' end of DNA fragments. The adapted fragments can be hybridized to poly-T oligonucleotides immobilized on the tSMS flow cell. The library members can be immobilized onto the flow cell at a density of about 100 million templates/cm$^2$. The flow cell can be then loaded into an instrument, e.g., HELISCOPE™ sequencer, and a laser can illuminate the surface of the flow cell, revealing the position of each template. A CCD camera can map the position of the templates on the flow cell surface. The library members can be subjected to repeated cycles of polymerase-directed single base extension. The sequencing reaction can begin by introducing a DNA polymerase and a fluorescently labeled nucleotide. The polymerase can incorporate the labeled nucleotides to the primer in a template directed manner. The polymerase and unincorporated nucleotides can be removed. The templates that have directed incorporation of the fluorescently labeled nucleotide can be discerned by imaging the flow cell surface. After imaging, a cleavage step can remove the fluorescent label, and the process can be repeated with other fluorescently labeled nucleotides until a desired read length is achieved. Sequence information can be collected with each nucleotide addition step.

The next generation sequencing technology can utilize a 454 (Roche) sequencing platform, for example as described in Margulies, M. et al. *Nature* 437:376-380 [2005]. 454 sequencing generally involves two steps. In a first step, DNA can be sheared into fragments. The fragments can be blunt-ended. Oligonucleotide adaptors can be ligated to the ends of the fragments. The adaptors generally serve as primers for amplification and sequencing of the fragments. At least one adaptor can comprise a capture reagent, e.g., a biotin. The fragments can be attached to DNA capture beads, e.g., streptavidin-coated beads. The fragments attached to the beads can be PCR amplified within droplets of an oil-water emulsion, resulting in multiple copies of clonally amplified DNA fragments on each bead. In a second step, the beads can be captured in wells, which can be pico-liter sized. Pyrosequencing can be performed on each DNA fragment in parallel. Pyrosequencing generally detects release of pyrophosphate (PPi) upon nucleotide incorporation. PPi can be converted to ATP by ATP sulfurylase in the presence of adenosine 5' phosphosulfate. Luciferase can use ATP to convert luciferin to oxyluciferin, thereby generating a light signal that is detected. A detected light signal can be used to identify the incorporated nucleotide. Similar to Ion Torrent, the 454 system can require libraries amplified by a separate emulsion PCR prior to any sequencing, which can complicate and slow down the sequencing process. This system can also yield a similarly high error rate (e.g., 0.5-1%; indel error rate of 0.4 per 100 base pairs). For example, the preparation and sequencing times for a Roche 454 GS sequencer with an GS Junior Plus configuration can be up to 8 hours and 18 hours, respectively. This setup can be expected to output anywhere from 50 to 70 megabytes of data per run, comprised of 700 base pair single nucleotide sequences. A similar setup using the Titanium XL+ configuration can have the same preparation time, but a higher a sequencing run of up to 30 hours. This setup can be expected to output anywhere from 100 to 120 gigabytes of data per run, comprised of the similar 700 base pair single nucleotide reads. Overall, the phred quality score (Q) for the reads in these systems ranges from 20 to 30, which translates to a sequencing accuracy of 99% to 99.9%, respectively.

The next generation sequencing technology can utilize SOLiD™ technology (Applied Biosystems). The SOLiD platform generally utilizes a sequencing-by-ligation approach. Library preparation for use with a SOLiD platform generally comprises ligation of adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations can be prepared in microreactors containing beads, primers, template, and PCR components. Following PCR, the templates can be denatured. Beads can be enriched for beads with extended templates. Templates on the selected beads can be subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide can be removed and the process can then be repeated.

The next generation sequencing technology can utilize a single molecule, real-time (SMRT™) sequencing platform (Pacific Biosciences). In SMRT sequencing, the continuous incorporation of dye-labeled nucleotides can be imaged during DNA synthesis. Single DNA polymerase molecules can be attached to the bottom surface of individual zero-mode wavelength identifiers (ZMW identifiers) that obtain sequence information while phospho-linked nucleotides are being incorporated into the growing primer strand. A ZMW generally refers to a confinement structure which enables observation of incorporation of a single nucleotide by DNA polymerase against a background of fluorescent nucleotides that rapidly diffuse in an out of the ZMW on a microsecond scale. By contrast, incorporation of a nucleotide generally occurs on a milliseconds timescale. During this time, the fluorescent label can be excited to produce a fluorescent signal, which is detected. Detection of the fluorescent signal can be used to generate sequence information. The fluorophore can then be removed, and the process repeated. Library preparation for the SMRT platform generally involves ligation of hairpin adaptors to the ends of DNA fragments. These ligated DNA fragments can vary in length up to, but not limited to, 40,000 base pairs depending on the desired output read-size (commonly referred as long reads). The average preparation time can involve approximately 8 hours, and does not require the alteration of DNA sequences for, or during, DNA polymerase synthesis—thus its ability to resolve repetitive genomic regions and potential DNA modifications (e.g., DNA methylation). Although a powerful technique, it can produce one of the highest error rates among next generation sequencing technologies: 14 percent. For example, using the SMRT™ platform with an RS II configuration it can run up to 4 hours and can produce 0.5 to 1 gigabytes of data per run, comprised of the long reads described above. Overall, the phred quality score (Q) for the reads in this system is mostly 30, which translates to a sequencing accuracy of 99.9%.

The next generation sequencing technology can utilize nanopore sequencing (e.g., as described in Soni GV and Meller A. Clin Chem 53: 1996-2001 [2007]). Nanopore sequencing DNA analysis techniques are being industrially developed by a number of companies, including but not limited to Oxford Nanopore Technologies (Oxford, United Kingdom). Nanopore sequencing is a single-molecule sequencing technology whereby a single molecule of DNA is sequenced directly as it passes through or adjacent to a nanopore. A nanopore can be a small hole, of the order of 1 nanometer in diameter. Immersion of a nanopore in a conducting fluid and application of a potential (voltage) across can result in a slight electrical current due to conduction of ions through the nanopore. The amount of current which flows is sensitive to the size and shape of the nanopore and to occlusion by, e.g., a DNA molecule. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Other nanopore-based detection modalities can also be employed. Nanopore sequencing can exhibit the highest error-rate for any sequencing technology at the moment, reaching up to, but not limited to, 25-30%. Nevertheless, current development has been focused on reducing this error rate, for example by sequencing through multiple dimensions. Initially sequencing in 1-D, Oxford Nanopore Technologies has expanded to 2-D sequencing that can yield a lower error-rate and increase the accuracy. Sequencing run-time can be dependent on the user, as the technology can continue reading the DNA molecule until the user requires, the flow cell is worn out, or more reagents or sample are needed.

The next generation sequencing technology can utilize a chemical-sensitive field effect transistor (chemFET) array (e.g., as described in U.S. Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

The next generation sequencing technology can utilize transmission electron microscopy (TEM). The method, termed Individual Molecule Placement Rapid Nano Transfer (IMPRNT), generally comprises single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

The method can utilize sequencing by hybridization (SBH). SBH generally comprises contacting a plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be identified and used to identify the plurality of polynucleotide sequences within the sample.

The length of the sequence read can vary depending on the particular sequencing technology utilized. NGS platforms can provide sequence reads that vary in size from tens to hundreds, or thousands of base pairs, or even tens or hundreds of thousands of base pairs. In some embodiments of the methods described herein, the sequence reads are about 20 bases long, about 25 bases long, about 30 bases long, about 35 bases long, about 40 bases long, about 45 bases long, about 50 bases long, about 55 bases long, about 60 bases long, about 65 bases long, about 70 bases long, about 75 bases long, about 80 bases long, about 85 bases long, about 90 bases long, about 95 bases long, about 100 bases long, about 110 bases long, about 120 bases long, about 130 bases long, about 140 bases long, about 150 bases long, about 200 bases long, about 250 bases long, about 300 bases long, about 350 bases long, about 400 bases long, about 450 bases long, about 500 bases long, about 600 bases long, about 700 bases long, about 800 bases long, about 900 bases long, about 1000 bases long, or more than 1000 bases long.

Partial sequencing of DNA fragments present in the sample can be performed.

Encryption

The methods and systems disclosed herein can also employ encryption. Encryption can be performed using a one-time pad cipher for encryption. Additional, non-limiting examples of encryption methods can include cryptographically secure pseudorandom number generators, information-theoretically secure algorithms, integer factorization algorithms, primality tests, advanced access content system, symmetric-key algorithms, broken cryptography algorithms, cryptanalytic algorithms, and cryptographic hash functions. Furthermore, the encryption methods can utilize key pair concepts that utilize a public key, private key and/or passphrase (similar to that used in secure e-mail transfer). For example, the encrypting analysis device may have the public key of the intended recipient device. Similarly, the intended recipient device may have to have the public key of the encrypting analysis device. A keyed-hash message authentication code (HMAC) can also be used to generate a message authentication code using a cryptographic hash function in combination with a secret cryptographic key. This message authentication code can be used to verify both data integrity as well as to authenticate the sequence or data being transmitted. When encryption keys are used for sending and receiving sequence data, the keys can, e.g., be generated randomly and can contain sufficient entropy. Entropy can be derived from unpredictable computer operations. For example, the movement of a disk drive head.

Encrypted information, such as sequence information, can be compared without decrypting.

Alternative encryption methods can be employed alone or in combination. For example, a digital signature can be generated using the private key of a key pair. The digital signature can confirm that the biological sequence being sent was signed by the sender.

Encryption can be conducted while a sequencer is conducting a sequencing assay. Techniques of the present disclosure can provide rapid computing that enables for analysis, encryption, and other processing on the time scale of a sequencing assay, including real-time analysis.

Computer Systems

A computer system can execute the methods disclosed herein using instructions contained in a non-transitory computer-readable medium. Non-transitory computer-readable media can in some instances comprise all computer-readable media except for a transitory, propagating signals.

In some embodiments, a processor is associated with one or more controllers, calculation units, and/or other units of a computer system, or implanted in firmware. In some embodiments, one or more steps of the method are implemented in hardware. In some embodiments, one or more steps of the method are implemented in software. Software routines may be stored in any computer readable memory unit such as flash memory, RAM, ROM, magnetic disk, laser disk, or other storage medium as described herein or known in the art. Software may be communicated to a computing device by any known communication method including, for example, over a communication channel such as a telephone line, the internet, a wireless connection, or by a transportable medium, such as a computer readable disk, flash drive, etc. The one or more steps of the methods described herein may be implemented as various operations, tools, blocks, modules and techniques which, in turn, may be implemented in firmware, hardware, software, or any combination of firmware, hardware, and software. When implemented in hardware, some or all of the blocks, operations, techniques, etc. may be implemented in, for example, an application specific integrated circuit (ASIC), custom integrated circuit (IC), field programmable logic array (FPGA), or programmable logic array (PLA).

A system can include a central computer server that is programmed to implement exemplary methods described herein. The server can include a central processing unit (CPU, also "processor") which can be a single core processor, a multi core processor, or plurality of processors for parallel processing. In some instances, the system comprises less than 10, 9, 8, 7, 6, 5, 4, 3, or less than 2 processors.

One compute thread is a minimal viable instructing unit on a processor. Multiple threads can exist within the same process, executing concurrently (one starting before others finish) and share resources such as memory. Sometimes, however, a compute thread is also used to define the processor itself. For example, if one processor is one physical core, but it may have 4 threads, or logical cores. Accordingly, as used herein a "compute thread" can be a processor or thread.

In some instances, the systems described herein can use multithreading. In some instances, the systems comprise multitasking operating systems. Multithreading is a widespread programming and execution model that allows multiple threads to exist within the context of a single process. These threads share the process's resources, but are able to execute independently. Multithreading can also be applied to a single process to enable parallel execution on a multiprocessing system.

The server can also include memory (e.g., random access memory, read-only memory, flash memory); electronic storage unit (e.g., hard disk); communications interface (e.g. network adaptor) for communicating with one or more other systems; and peripheral devices which may include cache, other memory, data storage, and/or electronic display adaptors. The memory, storage unit, interface, and peripheral devices can be in communication with the processor through a communications bus, such as a motherboard. The storage unit can be a data storage unit for storing data. The server can be operatively coupled to a computer network ("network") with the aid of the communications interface. The network can be the Internet, an intranet and/or an extranet, an intranet and/or extranet that is in communication with the Internet, a telecommunication or data network. The network in some cases, with the aid of the server, can implement a peer-to-peer network, which may enable devices coupled to the server to behave as a client or a server.

The storage unit can store files, such as subject reports, and/or communications with the caregiver, sequencing data, data about individuals, or any aspect of data associated with the present disclosure.

The server can communicate with one or more remote computer systems through the network. The one or more remote computer systems may be, for example, personal computers, laptops, tablets, telephones, Smart phones, or personal digital assistants.

In some situations, the system includes a single server. In other situations, the system includes multiple servers in communication with one another through an intranet, extranet and/or the Internet.

The server can be adapted to store sequencing information, client or patient information, such as, for example, raw sequencing data, compressed sequence data, graphs containing sequence data, reference genomes, reference genomes comprising alternate paths, polymorphisms, mutations, patient history and demographic data and/or other information of potential relevance. Such information can be stored on the storage unit or the server and such data can be transmitted through a network.

Methods as described herein can be implemented by way of machine (or computer processor) executable code (or software) stored on an electronic storage location of the server, such as, for example, on the memory, or electronic storage unit. During use, the code can be executed by the processor. In some cases, the code can be retrieved from the storage unit and stored on the memory for ready access by the processor. In some situations, the electronic storage unit can be precluded, and machine-executable instructions are stored on memory. In some situations, the code can be executed on a second computer system.

Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software.

Non-volatile storage media can include, for example, optical or magnetic disks, such as any of the storage devices in any computer(s) or the like, such may be used to implement the system. Tangible transmission media can include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

A computer system may be used for one or more steps, including, e.g., sample collection, sample processing, sequencing, sequence comparison to a reference genome, sequence alignment, out putting to a graphical interface, generating a report, and reporting results to a receiver.

A client-server and/or relational database architecture can be used in the techniques of the present disclosure. In general, a client-server architecture is a network architecture in which each computer or process on the network is either a client or a server. Server computers can be powerful computers dedicated to managing disk drives (file servers), printers (print servers), or network traffic (network servers). Client computers can include PCs (personal computers) or workstations on which users run applications, as well as example output devices as disclosed herein. Client computers can rely on server computers for resources, such as files, devices, and even processing power. The server computer handles all of the database functionality. The client computer can have software that handles front-end data management and receive data input from users.

After performing a calculation, a processor can provide the output, such as from a calculation, back to, for example, the input device or storage unit, to another storage unit of the same or different computer system, or to an output device. Output from the processor can be displayed by a data display, e.g., a display screen (for example, a monitor or a screen on a digital device), a print-out, a data signal (for example, a packet), a graphical user interface (for example, a webpage), an alarm (for example, a flashing light or a sound), or a combination of any of the above. In an embodiment, an output is transmitted over a network (for example, a wireless network) to an output device. The output device can be used by a user to receive the output from the data-processing computer system. After an output has been received by a user, the user can determine a course of action, or can carry out a course of action, such as a medical treatment when the user is medical personnel. In some embodiments, an output device is the same device as the input device. Example output devices include, but are not limited to, a telephone, a wireless telephone, a mobile phone, a PDA, a flash memory drive, a light source, a sound generator, a fax machine, a computer, a computer monitor, a printer, an iPod, and a webpage. The user station may be in communication with a printer or a display monitor to output the information processed by the server. Such displays, output devices, and user stations can be used to provide an alert to the subject or to a caregiver thereof.

Data relating to the present disclosure can be transmitted over a network or connections for reception and/or review by a receiver. The receiver can be but is not limited to the subject to whom the report pertains; or to a caregiver thereof, e.g., a health care provider, manager, other healthcare professional, or other caretaker; a person or entity that performed and/or ordered the genotyping analysis; a genetic counselor. The receiver can also be a local or remote system for storing such reports (e.g. servers or other systems of a "cloud computing" architecture). In one embodiment, a computer-readable medium includes a medium suitable for transmission of a result of an analysis of a biological sample.

A sequence graph stored in an explicit way for the human genome can require 40 GB of storage. The minimal data structure for explicit sequence graph storage with a sequence of length N and M alternate paths, capable of holding the human reference genome and the variants from the 1000 genomes phase III call set, goes as $$N * 13 \text{ Bytes} + \sum_{k=0}^{number\ of\ variants} (\text{length of variant } k) * 13 \text{ Bytes} + 16 \text{ Bytes},$$

where each nucleotide on the reference has a minimally sized associated node ID and edge and each alternate path has corresponding pointers to the reference node ID and edge. In techniques of the present disclosure, storage of the sequence graph can be as $$N + \sum_{k=0}^{number\ of\ variants} (\text{length of variant } k) + 8 \text{ Bytes}$$

where each nucleotide on the reference is minimally stored in a single Byte and each nucleotide on the alternate path is stored in a single byte. Further, each alternate path can contain a start position and an end position. With this data structure, the human linear reference and 1000 genomes phase III call set can require under 3.5 GB of storage, an order of magnitude less than the current industry standards.

The techniques of the present disclosure can be applied to other sequences, such as bacteria. For example, in the case of Mycobacterium Tuberculosis, using H37Rv as a reference, and Mycobacterium canettii for the alternate paths, the current industry practice would generate a graph of at least 55 megabytes, whereas the enclosed invention can generate a graph about 4.5 megabytes in size.

A k-mer index constructed on the aforementioned industry standard graph, minimally 40 GB in size, was ultimately deemed too large (>500GB) to continue using and various alternatives employing Burrows Wheeler transforms, combined with compression techniques, were explored by the industry. These techniques represented alternative ways to extract the same information, through transformations, but the techniques of the present disclosure can circumvent this large index, for example because of the efficient sequence graph storage. With the invention's sequence graphs, and a k-mer index of said graph, alternatively masked k-mers, the k-mer index of the whole human reference genome with the 1000 genomes phase III call set can fit in under 72 GB of computer storage (e.g., using a k-mer mask size of 33).

By storing each k-mer in base 4, along with the offset, and a unique pointer for each alternate path pointing to a data structure containing the sequence, start offset, and end offset of the alternate path, the index grows as $$\left( N - k + k * \sum_{j=0}^{number\ of\ variants} (k + (length\ of\ variant\ j) - 1) \right) * 16\ Bytes,$$

where N is the length of the reference sequence and k is the length of the mask used to generate the k-mer. The mask can be a string of '1's and represent a perfect match to the reference sequence graph, or a mask can contain '0's, which exclude the base it masks from the k-mer. For the human reference chromosome 1 sequence with 1000 genomes as alternate paths, and assuming each alternate is a single SNP, the masked k-mer index can be 3.98 GB in size. Therefore, in one example, techniques of the present disclosure can generate a masked k-mer index that grows at a rate of 16 Bytes per base in the reference and 528 Bytes per variant.

This index can then be used to find candidate alignment locations of sequences to align back on the sequence graph. K-mers of the sequence to align can be generated (for example, at a rate of 40,642 sequences/sec/compute thread) and searched for in the index. Some k-mers can point to the reference sequence; some can point to alternate paths.

BFAST can treat every k-mer as a candidate alignment location (CAL), which yields several equivalent CALs and spurious CALs. In order to avoid this, the k-mer positions can be normalized so that the equivalent CALs are merged, or synchronized, into a single CAL, resulting in fewer CALs that need to be tested in the alignment module. The k-mers can each have a relative offset to the reference sequence; this can be subtracted to the offset in the reference sequence to obtain the normalized offset.

FIG. 6 shows an exemplary candidate alignment location generation and read graph alignment workflow. FIG. 6A shows a sequence receiving module 600 that gets the sequence to be aligned 601. FIG. 6B shows a k-mer-izing module 610 that applies the mask to obtain the k-mer decomposition of the sequence 611. FIG. 6C shows a graph index query module 620 that finds k-mers 621 in the reference graph 622. FIG. 6D shows a k-mer graph synchronization module 630 that synchronizes compatible k-mers into a single candidate alignment location 631. FIG. 6E shows a graph seeding module 640 that generate seeds 641 by taking the longest covered section from the sequence. FIG. 6F shows a graph alignment module 650 that performs graph alignment by extending the seed into the graph 651 using dynamic programming algorithms.

Some k-mers are directly compatible and some k-mers are indirectly compatible, as shown for example in FIG. 7. Two k-mers with the same normalized offset (dotted arrow) are directly compatible if both belong to the reference sequence or both belong to the same alternate path; they are incompatible when one belongs to the reference sequence and the other to an alternate path. FIG. 7A shows an example where both k-mers have the same normalized offset and belong to the reference sequence: directly compatible. FIG. 7B shows an example where both k-mers have the same normalized offset and belong to the same alternate path: directly compatible. FIG. 7C shows an example where both k-mers belong to the reference sequence but have different normalized offsets: directly incompatible. FIG. 7D shows an example where one k-mer belongs to the reference sequence, the other to an alternate path, and both have the same normalized offset: indirectly compatible. FIG. 7E shows an example where both k-mers have the same normalized offset but belong to different alternate paths: indirectly incompatible. Directly compatible k-mers belong to the same reference path or alternate path and have the same normalized offset (see, e.g., FIG. 7A). Indirectly compatible k-mers are k-mers from the sequence to be aligned wherein some k-mers point to the reference sequence and some k-mers point to an alternate path, but the set of k-mers have the same normalized offset (see, e.g., FIG. 7C). The normalized offset is the candidate alignment location of the read supported by the compatible k-mers (see, e.g., FIG. 6D). FIG. 8 shows exemplary schematics illustrating offset normalization to reduce the number of candidate alignment locations (CALs). In FIG. 8A, the sequence to be aligned 801 is split into smaller k-mers 802, each with its relative offset with respect to the sequence. In FIG. 8B, the second group of k-mers 803 form a single candidate alignment location.

Figure 9:
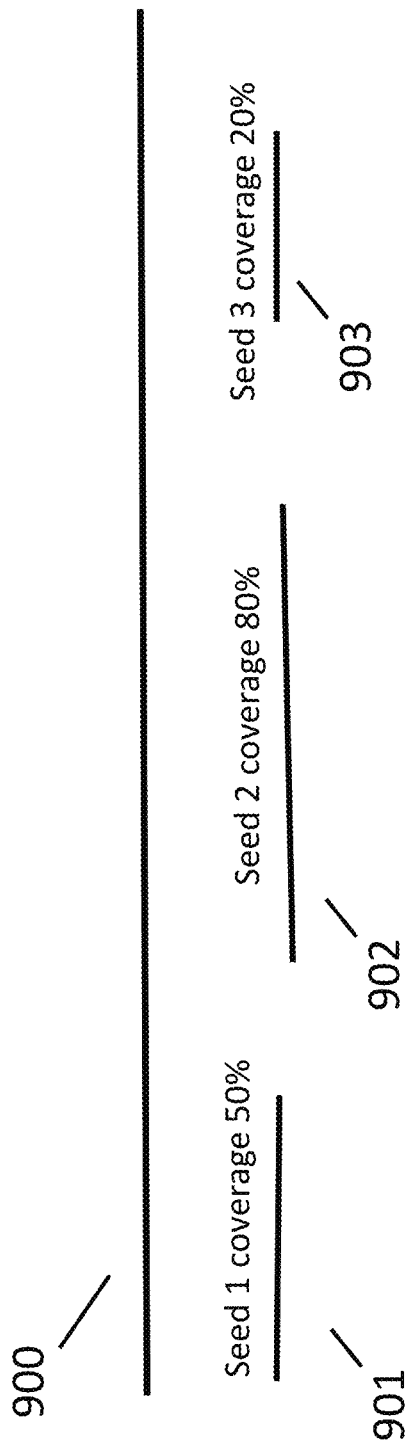
FIG. 9 shows an exemplary process for determining the seed to use to begin dynamic programming or alignment to the sequence graph.

FIG. 9 shows an exemplary process for determining the seed to use to begin dynamic programming or alignment to the sequence graph 900. Due to the large amount of candidate alignment locations that can be generated from a sequence, it may be undesirable or impossible to run all of them through the graph alignment module. For this reason, the best seeds can be heuristically selected by ranking them using the total coverage. For example, Seed 1 901 has 50% coverage, Seed 2 902 has 80% coverage, and Seed 3 903 has 20% coverage; Seed 2 can be selected as the best.

Within the enclosed storage schemes and data structures to represent the sequence graph, k-mers in the index can be queried at a rate of greater than or equal to 1,000, 2,000, 3,000, 4,000, 5000, 6,000, 7,000, 8,000, 9,000, 10,000, 15,000, 20,000, 25,000, 30,000, 35,000, 40,000, 45,000, 50,000, 55,000, 60,000 65,000, 66,000, 67,000,68,000, 69,000, 70,000, 75,000, 80,000, 85,000, 90,000, 95,000, 100,000, 105,000, 110,000, 115,000, 120,000, 125,000, 130,000, 135,000, 140,000, 145,000, 150,000, 155,000, 160,000, 165,000, 170,000, 175,000, 180,000, 185,000, 190,000, 195,000, 200,000, 205,000, 210,000, 215,000, 220,000, 225,000, 230,000, 235,000, 240,000, 245,000, 250,000, 255,000, 260,000, 265,000, 270,000, 275,000, 280,000, 285,000, 290,000, 295,000, 300,000, 305,000, 310,000, 315,000, 320,000, 325,000, 330,000, 335,000, 340,000, 345,000, 350,000, or 355,000 k-mers/second per compute thread. In some embodiments, using these data structures, k-mers from the sequences to align can be queried in the sequence graph index at a rate of greater than or equal to 355,000 k-mers/second/compute thread. Alternative k-mer indexes built on industry standard explicit graph indexes can be queried at a rate of 70-1000 k-mers/sec/compute thread.

Figure 6A:
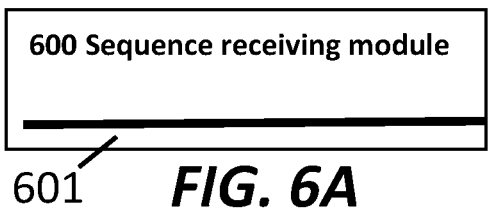
FIG. 6A, FIG. 6B, FIG. 6C, FIG. 6D, FIG. 6E, and FIG. 6F show an exemplary candidate alignment location (CAL) generation and read graph alignment workflow.
Figure 6B:
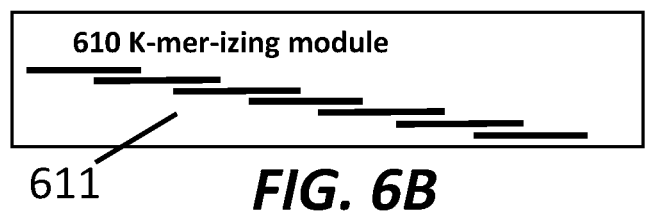
Figure 6C:
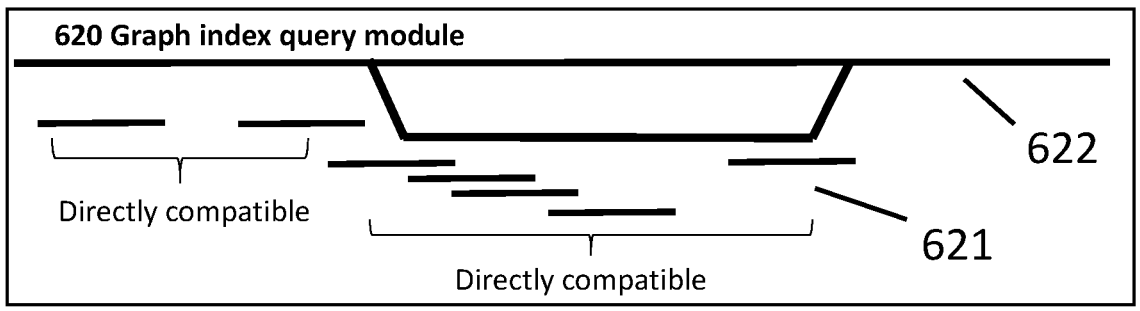
Figure 6D:
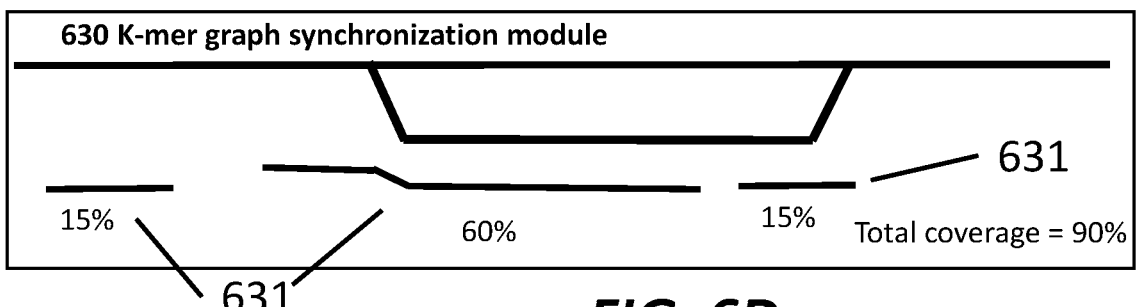
Figure 6E:
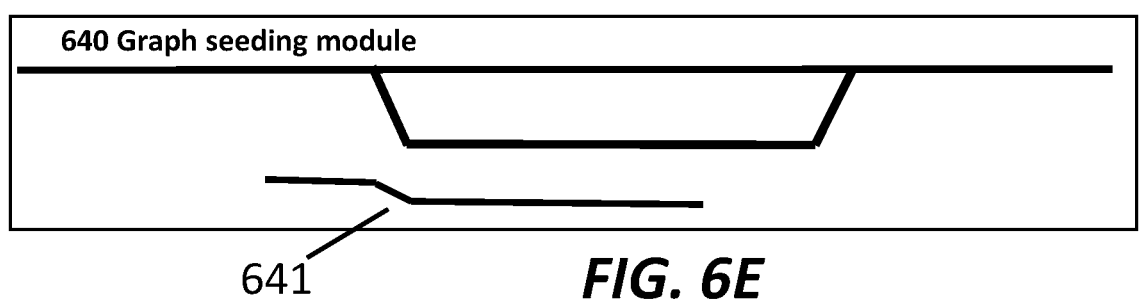
Figure 6F:
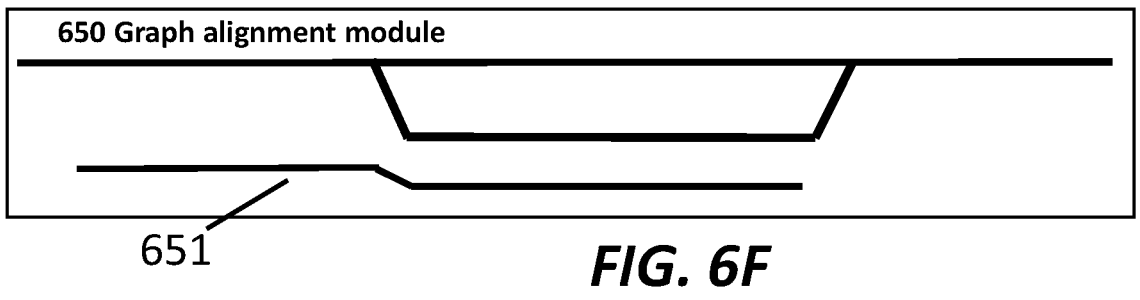
Figure 7A:
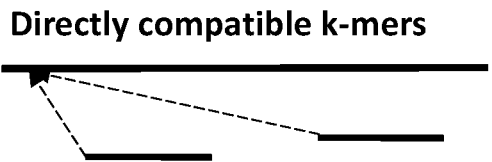
FIG. 7A, FIG. 7B, FIG. 7C, FIG. 7D, and FIG. 7E show exemplary definitions for k-mer compatibility or incompatibility.
Figure 7B:
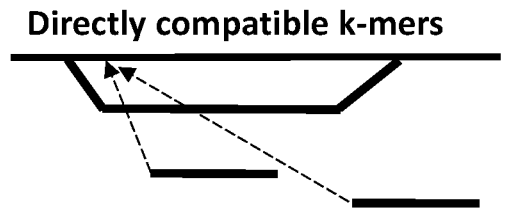
Figure 7C:
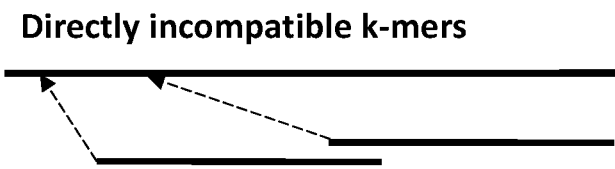
Figure 7D:
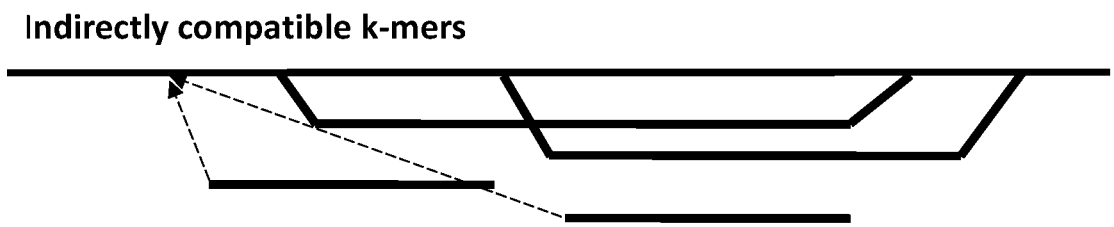
Figure 7E:
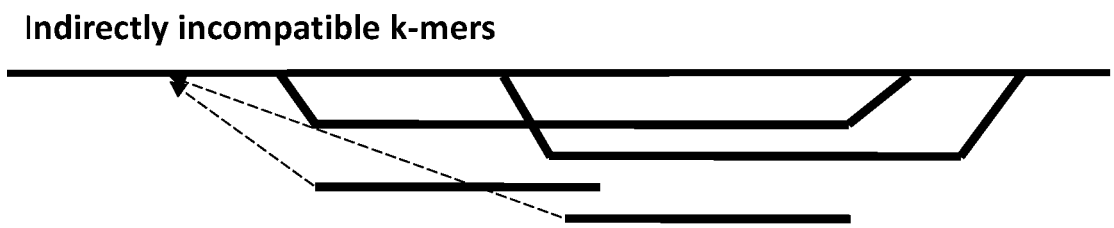

After k-mers have been placed in the reference sequence graph, the normalized offset has been computed for each, and the sequence has candidate alignment locations, the longest coverage of bases along the reference sequence graph, as determined by the sum of the bases covered by the k-mers, can be used to seed the sequence in the graph (see, e.g., FIG. 6E). In one example, by using these data structures, sequences can be seeded at a rate of 8704 sequences/sec/compute thread, including the time for k-mer synchronization. Sequences can be seeded at a rate of greater than or equal to about 100, 200, 300, 400, 500, 600, 700, 800, 900, 1000,1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 sequences/sec/compute thread, including the time for k-mer synchronization.

Candidate alignment locations can be ranked so that the ones with the highest coverage will be passed to the graph alignment module (see, e.g., FIG. 9). In one example, by aligning a single seed per sequence, the sequences are aligned at a rate of 13,754 reads/sec/compute thread. In one example, by aligning at most 5 seeds per sequence, the sequences are aligned at a rate of 4,607 reads/sec/compute thread. In one example, by aligning at most 32 seeds per sequence, the sequences are aligned at a rate of 978 reads/sec/compute thread.

Table 1 shows the sensitivity and true discovery rate (i.e., 1—false discovery rate) of the current graph-based methods disclosed herein compared to a state-of-the-art linear aligner. These results were generated from a simulation of chromosome 1 using VarSim at 30X coverage. The results show an improvement of 0.9% for the true discovery rate, and a 0.4% difference for the sensitivity with respect to BWA.

TABLE 1

Sensitivity and True Discovery Rate

| METHOD | SENSITIVITY (%) | TRUE DISCOVERY RATE (%) |
| --- | --- | --- |
| BWA | 98.3 | 96.1 |
| GRAPH-BASED METHOD | 97.9 | 97.0 |

Figure 4:
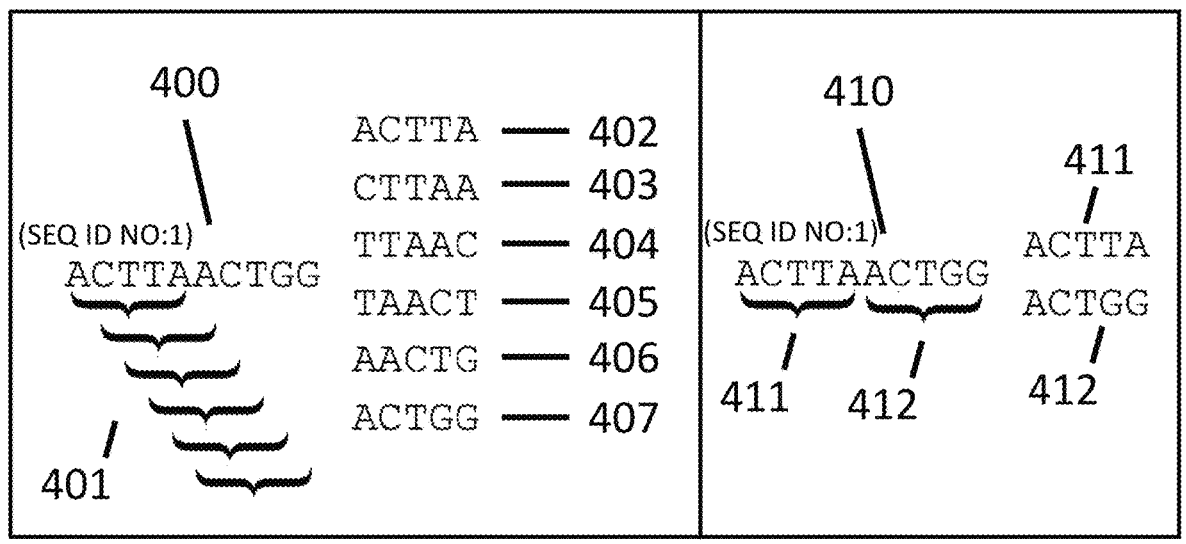
FIG. 4 shows an example of two k-mer profiles of a sequence.

A k-mer profile can represent a sequence broken into its k-elements, or k-mers. In some cases, a profile represents the set of k-mers can represent breaking up the sequence into k-mers every other element sequence. In some cases, the k-mer profile can involve the division of k-mers into the smallest number of elements it can have. For example, FIG. 4 shows two exemplary ways to have a k-mer profile of a sequence. On the left hand side, a sequence 400 is broken up 401 into six k-mers 402 403 404 405 406 407, each of a size of 5 and added sequentially. On the right, the same sequence 410 is broken up into two non-overlapping k-mers 411 412.

Techniques of the present disclosure can be used to retrieve a read, generate a k-mer profile from this read, and query the profile to an index of k-mer profiles from a reference sequence with alternate paths to call variants. In some cases, the querying can be used to detect a specific fragment of a sequence. In some cases, it can be used to query the presence of a variant.

FIG. 5 shows an example of a reference 501 and the alternate paths 502, along with their IDs 503. In some cases, the alternate paths are referred to as bubbles. A variety of additional read tags 504 can be used. A 'VL' tag can be used which mentions the alternate paths that the read crossed. A 'VN' tag can also be used to detail how many variants the read passes through. An 'NL' tag can be used to detail the reference paths that align to the bubble (e.g., that it did not pass through the alternate path). A 'VV' read tag can be used to detail the reads that start to map at the variant. A 'GD' tag can contain alignment scores including, but not limited to, number of matches, mismatches, insertions, deletions, and start position related to the variant path. A 'GR' tag can indicate both the start and end of the aligned read relative to the coordinate of the variant path.

As a k-mer profile passes through the index of a reference sequence with alternate paths, the system can query if a k-mer is present in an alternate path. In some cases, this is enough evidence to call the variants. In other cases, only k-mers with a high quality score can be attributed to the variant. In other cases, the variant can be chosen using a statistical model.

In some cases, the k-mer profile formation can include gapped k-mers, as well as the formation of the index of the paths.

In some cases, the k-mer index can condense sequences at a rate of up to 1 every 1,000 bases; in others it can condense 1 in 1,000,000 bases. In others, it can condense 1 in 10,000,000 or more bases.

The k-mer index can include phased information to create concise alternate paths.

In some cases, the k-mers of the index related to the alternate paths and its corresponding reference (i.e., the bubbles) are used, while the rest of the index is discarded. In some cases, this reduces the size of the k-mer index by more than 99%. In some cases, it is more than 99.9%. Reducing the k-mer space to this size can highlight the difference between variants, subspecies and different sequences. In some cases, this can accelerate the querying process more than 1.1×, 1.2×, 1.3×, 1.4×, 1.5×, 1.6×, 1.7×, 1.8×, 1.9×, 2×, 3×, 4×, 5×, 6×, 7×, 8×, 9×, 10×, 20×, 30×, 40×, 50×, 60×, 70×, 80×, 90×, 100×, 200×, 300×, 400×, 500×, 600×, 700×, 800×, 900×, or 1000× k-mers per second.

In some cases, calling variants is performed using an index where only the alternate paths and its corresponding reference (i.e., the bubbles) are used, while the rest of the index can be discarded. This can accelerate the variant calling process more than 1.1×, 1.2×, 1.3×, 1.4×, 1.5×, 1.6×, 1.7×, 1.8×, 1.9×, 2×, 3×, 4×, 5×, 6×, 7×, 8×, 9×, 10×, 20×, 30×, 40×, 50×, 60×, 70×, 80×, 90×, 100×, 200×, 300×, 400×, 500×, 600×, 700×, 800×, 900×, or 1000× k-mers per second.

K-mers can be size 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100 or higher.

The present invention has been described in terms of one or more preferred embodiments, and it should be appreciated that many equivalents, alternatives, variations, and modifications, aside from those expressly stated, are possible and within the scope of the invention.

We claim:

1. A method to identify novel variants, the method comprising:
   (a) obtaining, using a hardware processor, a plurality of sequence reads;
   (b) aligning, using the hardware processor, the plurality of sequence reads against a graph reference comprising a plurality of alternate paths that each represents a known variant, wherein the aligning comprises:
   generating, using the hardware processor, a k-mer profile from each of the plurality of sequence reads; and
   querying, using the hardware processor, each k-mer profile to an index of k-mer profiles generated from the graph reference,
   wherein each k-mer in the index of k-mer profiles that corresponds to at least one alternate path is stored with a unique pointer for each of the at least one alternate paths that points to a data structure associated with that alternate path, the data structure including a sequence associated with the alternate path,
   and a start offset and an end offset indicative of a location of the alternate path with respect to the graph reference; and
   (c) using a subset of the plurality of sequence reads which abnormally align against one or more of the plurality of alternate paths to identify novel variants.

2. The method of claim 1, wherein the novel variants comprise structural variants.

3. The method of claim 1, wherein the subset of the plurality of sequence reads used to identify novel variants aligns abnormally to all alternate paths in the graph reference.

4. The method of claim 1, wherein the sequence reads comprise read pairs, and wherein abnormal alignment comprises an aligned read pair orientation different from that of a majority of aligned read pairs.

5. The method of claim 1, wherein the sequence reads comprise read pairs, and wherein abnormal alignment comprises an aligned read pair insert length that is smaller or larger than that of a majority of the aligned read pairs.

6. The method of claim 5, wherein the insert length is more than 10% larger or smaller than the median insert length of a subset of the aligned reads.

7. The method of claim 5 wherein the insert length is larger or smaller than some user-specified value.

8. The method of claim 1, wherein the sequence reads comprise read pairs, and wherein abnormal alignment comprises a read pair in which one read is aligned and one read is unaligned.

9. The method of claim 1, wherein abnormal alignment comprises a read in which part of the read is clipped.

10. The method of claim 1, further comprising:
automatically adding a subset of the identified novel variants to the graph reference to produce an updated graph reference; and
using the updated graph reference for another alignment.

11. The method of claim 10, further comprising counting a number of reads that align to one or more alternate paths in the graph reference and using the number of reads that align to one or more alternate paths in the graph reference to identify the known variants.

12. The method of claim 10, wherein the identified novel variants comprise structural variants.

13. The method of claim 10, wherein abnormal alignment comprises one or more of the following:
a) an aligned read pair orientation different from that of a majority of aligned read pairs;
b) an aligned read pair insert length that is smaller or larger than that of a majority of aligned read pairs;
c) a read pair in which one read is aligned and one read is unaligned;
d) a read in which a part of the read is clipped;
e) a read pair in which an insert length is larger than the 99th percentile or smaller than the 1st percentile of insert lengths of a subset of aligned read pairs; and
f) a read pair in which reads align to different reference sequences.

14. The method of claim 10, further comprising identifying a subset of the identified novel variants that satisfy predefined quality measures or detection certainty measures and adding the subset to the graph reference.

15. The method of claim 14, wherein the predefined quality measures or detection certainty measures comprise one or more of the following: (i) a predefined size range, (ii) a predefined region of a genome, and (iii) a detection frequency.

16. The method of claim 10, further comprising:
using the graph reference in more than one alignment and variant detection; and
progressively updating the graph reference based on the more than one alignment and variant detection.

17. The method of claim 1, wherein the known variants or the novel variants comprise intra-species variants.

18. The method of claim 1, wherein the known variants or the novel variants comprise inter-species variants.

19. A method for calling variants, the method comprising:
(a) retrieving, using a hardware processor, a sequencing read generated from a sample by a sequencing device;
(b) generating, using the hardware processor, a k-mer profile from the read using a mask containing 1's and one or more 0's to generate each k-mer from the sequencing read such that bases in the read corresponding to the one or more 0's are excluded from the k-mer;
(c) querying, using the hardware processor, the k-mer profile to an index of k-mer profiles, generated from a reference sequence with alternate paths using the mask, to call variants,
wherein each k-mer in the index of k-mer profiles that corresponds to at least one alternate path is stored with a unique pointer for each of the at least one alternate paths that points to a data structure associated with that alternate path, the data structure including a sequence associated with the alternate path, and a start offset and an end offset indicative of a location of the alternate path with respect to the reference sequence; and
(d) determining, using the hardware processor, a species or a strain present in the sample based on the called variants.

20. The method of claim 19, wherein the variants comprise novel variants.

21. The method of claim 20, further comprising:
automatically adding a subset of the novel variants to the index to produce an updated index; and
using the updated index for another query.

22. The method of claim 21, further comprising:
using the updated index for more than one query and variant detection; and
progressively updating the updated index based on the more than one query and variant detection.

* * * * *

SEQUENCE LISTING

<160> NUMBER OF SEQ ID NOS: 12

<210> SEQ ID NO 1
<211> LENGTH: 10
<212> TYPE: DNA

```
<213> ORGANISM: Artificial Sequence
<220> FEATURE:
<223> OTHER INFORMATION: synthetic

<400> SEQUENCE: 1
acttaactgg                                                          10

<210> SEQ ID NO 2
<211> LENGTH: 45
<212> TYPE: DNA
<213> ORGANISM: Artificial Sequence
<220> FEATURE:
<223> OTHER INFORMATION: synthetic

<400> SEQUENCE: 2
agcatgttag ataagatagc tgtgctagta ggcagtcagc gccat                   45

<210> SEQ ID NO 3
<211> LENGTH: 17
<212> TYPE: DNA
<213> ORGANISM: Artificial Sequence
<220> FEATURE:
<223> OTHER INFORMATION: synthetic

<400> SEQUENCE: 3
ttagataaag gatactg                                                  17

<210> SEQ ID NO 4
<211> LENGTH: 14
<212> TYPE: DNA
<213> ORGANISM: Artificial Sequence
<220> FEATURE:
<223> OTHER INFORMATION: synthetic

<400> SEQUENCE: 4
aaaagataag gata                                                     14

<210> SEQ ID NO 5
<211> LENGTH: 11
<212> TYPE: DNA
<213> ORGANISM: Artificial Sequence
<220> FEATURE:
<223> OTHER INFORMATION: synthetic

<400> SEQUENCE: 5
gcctaagcta a                                                        11

<210> SEQ ID NO 6
<211> LENGTH: 17
<212> TYPE: DNA
<213> ORGANISM: Artificial Sequence
<220> FEATURE:
<223> OTHER INFORMATION: synthetic

<400> SEQUENCE: 6
ttagataaag gatactg                                                  17

<210> SEQ ID NO 7
<211> LENGTH: 14
<212> TYPE: DNA
<213> ORGANISM: Artificial Sequence
<220> FEATURE:
<223> OTHER INFORMATION: synthetic

<400> SEQUENCE: 7
aaaagataag gata                                                     14
```

```
<210> SEQ ID NO 8
<211> LENGTH: 11
<212> TYPE: DNA
<213> ORGANISM: Artificial Sequence
<220> FEATURE:
<223> OTHER INFORMATION: synthetic

<400> SEQUENCE: 8
gcctaagcta a                                                             11

<210> SEQ ID NO 9
<211> LENGTH: 11
<212> TYPE: DNA
<213> ORGANISM: Artificial Sequence
<220> FEATURE:
<223> OTHER INFORMATION: synthetic

<400> SEQUENCE: 9
atagcttcag c                                                             11

<210> SEQ ID NO 10
<211> LENGTH: 11
<212> TYPE: DNA
<213> ORGANISM: Artificial Sequence
<220> FEATURE:
<223> OTHER INFORMATION: synthetic

<400> SEQUENCE: 10
gctgcttagg c                                                             11

<210> SEQ ID NO 11
<211> LENGTH: 11
<212> TYPE: DNA
<213> ORGANISM: Artificial Sequence
<220> FEATURE:
<223> OTHER INFORMATION: synthetic

<400> SEQUENCE: 11
aatgaacaat g                                                             11

<210> SEQ ID NO 12
<211> LENGTH: 21
<212> TYPE: DNA
<213> ORGANISM: Artificial Sequence
<220> FEATURE:
<223> OTHER INFORMATION: synthetic

<400> SEQUENCE: 12
ggggcaggta atgaacgacg g                                                  21
```